United States Patent
Nitta

(10) Patent No.: US 12,268,446 B2
(45) Date of Patent: Apr. 8, 2025

(54) OPHTHALMIC APPARATUS AND OPHTHALMIC SYSTEM

(71) Applicant: Topcon Corporation, Tokyo (JP)

(72) Inventor: Sho Nitta, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 563 days.

(21) Appl. No.: 17/568,717

(22) Filed: Jan. 5, 2022

(65) Prior Publication Data

US 2022/0125307 A1 Apr. 28, 2022

Related U.S. Application Data

(63) Continuation of application No. PCT/JP2020/030484, filed on Aug. 7, 2020.
(Continued)

(51) Int. Cl.
*A61B 3/10* (2006.01)
*A61B 3/00* (2006.01)
*A61B 3/14* (2006.01)

(52) U.S. Cl.
CPC .......... *A61B 3/1025* (2013.01); *A61B 3/0008* (2013.01); *A61B 3/14* (2013.01)

(58) Field of Classification Search
CPC ....... A61B 3/1025; A61B 3/0008; A61B 3/14; A61B 3/1208; A61B 3/12; A61B 3/0016; A61B 3/1216
(Continued)

(56) References Cited

U.S. PATENT DOCUMENTS 7,331,669 B2   2/2008 Elsner
7,465,049 B2   12/2008 Maeda et al.
(Continued)

FOREIGN PATENT DOCUMENTS

JP   S55-29316 A    3/1980
JP   61-293430 A   12/1986
(Continued)

OTHER PUBLICATIONS

International Search Report and Written Opinion mailed on Oct. 20, 2020, received for PCT Application PCT/JP2020/030484, Filed on Aug. 7, 2020, 10 pages including English Translation.
(Continued)

*Primary Examiner* — Mahidere S Sahle
(74) *Attorney, Agent, or Firm* — XSENSUS LLP

(57) ABSTRACT

An ophthalmic apparatus includes an objective lens, an illumination optical system, a mounting unit, an imaging optical system, a communication unit, and a controller. The illumination optical system is configured to generate illumination light using light from a light source, and to illuminate a subject's eye with the illumination light through the objective lens. The mounting unit is configured to allow an external device including a sensor to be mounted so that the sensor is arranged on an imaging optical path. The imaging optical system is configured to guide returning light of the illumination light from the subject's eye to the imaging optical path. The communication unit has a communication function with the external device. The controller is configured to control the illumination optical system and to control the sensor through the communication unit to synchronize with control for the illumination optical system.

18 Claims, 20 Drawing Sheets

Related U.S. Application Data

(60) Provisional application No. 62/898,961, filed on Sep. 11, 2019.

(58) Field of Classification Search
USPC .......................................... 351/205, 206, 214
See application file for complete search history.

(56) References Cited

U.S. PATENT DOCUMENTS

| | | |
|---|---|---|
| 7,831,106 B2 | 11/2010 | Elsner et al. |
| 8,237,835 B1 | 8/2012 | Muller |
| 8,488,895 B2 | 7/2013 | Muller et al. |
| 11,096,573 B1 * | 8/2021 | Wallace ................ A61B 5/0077 |
| 2009/0244482 A1 | 10/2009 | Elsner et al. |
| 2010/0128221 A1 | 5/2010 | Muller et al. |
| 2015/0085252 A1 | 3/2015 | Fujimura et al. |
| 2016/0334610 A1 | 11/2016 | Kang et al. |
| 2016/0345822 A1 | 12/2016 | Fujimura et al. |
| 2021/0059522 A1 | 3/2021 | Shimizu et al. |

FOREIGN PATENT DOCUMENTS

| | | |
|---|---|---|
| JP | 2009-538697 A | 11/2009 |
| JP | 2010-259495 A | 11/2010 |
| JP | 2013-248376 A | 12/2013 |
| JP | 2016-202999 A | 12/2016 |
| JP | 2019-58437 A | 4/2019 |
| JP | 2019-83880 A | 6/2019 |
| WO | 2019/146792 A1 | 8/2019 |

OTHER PUBLICATIONS

Office Action issued on Aug. 22, 2023, in corresponding Japanese patent Application No. 2021-545168, 6 pages.
Japanese Office Action issued Jan. 24, 2023, in corresponding Japanese Patent Application 2021-545168, 8pp.

* cited by examiner

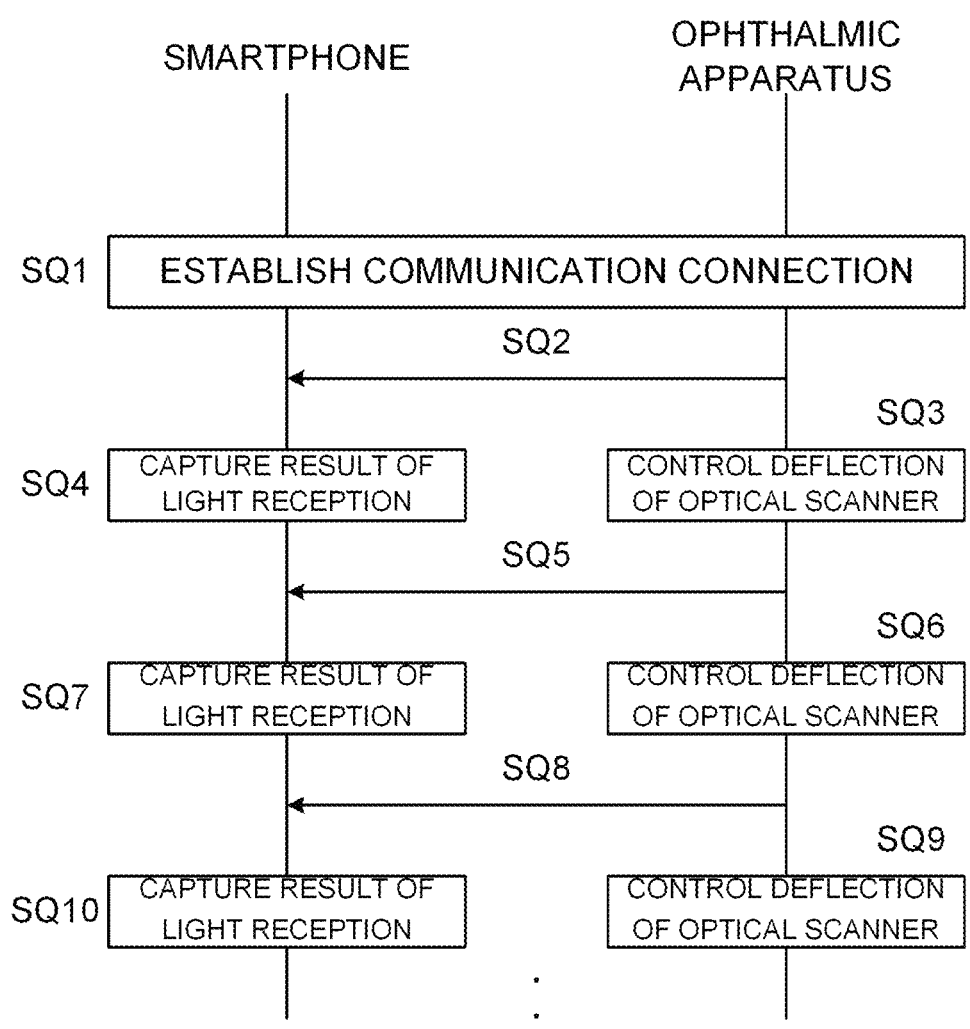

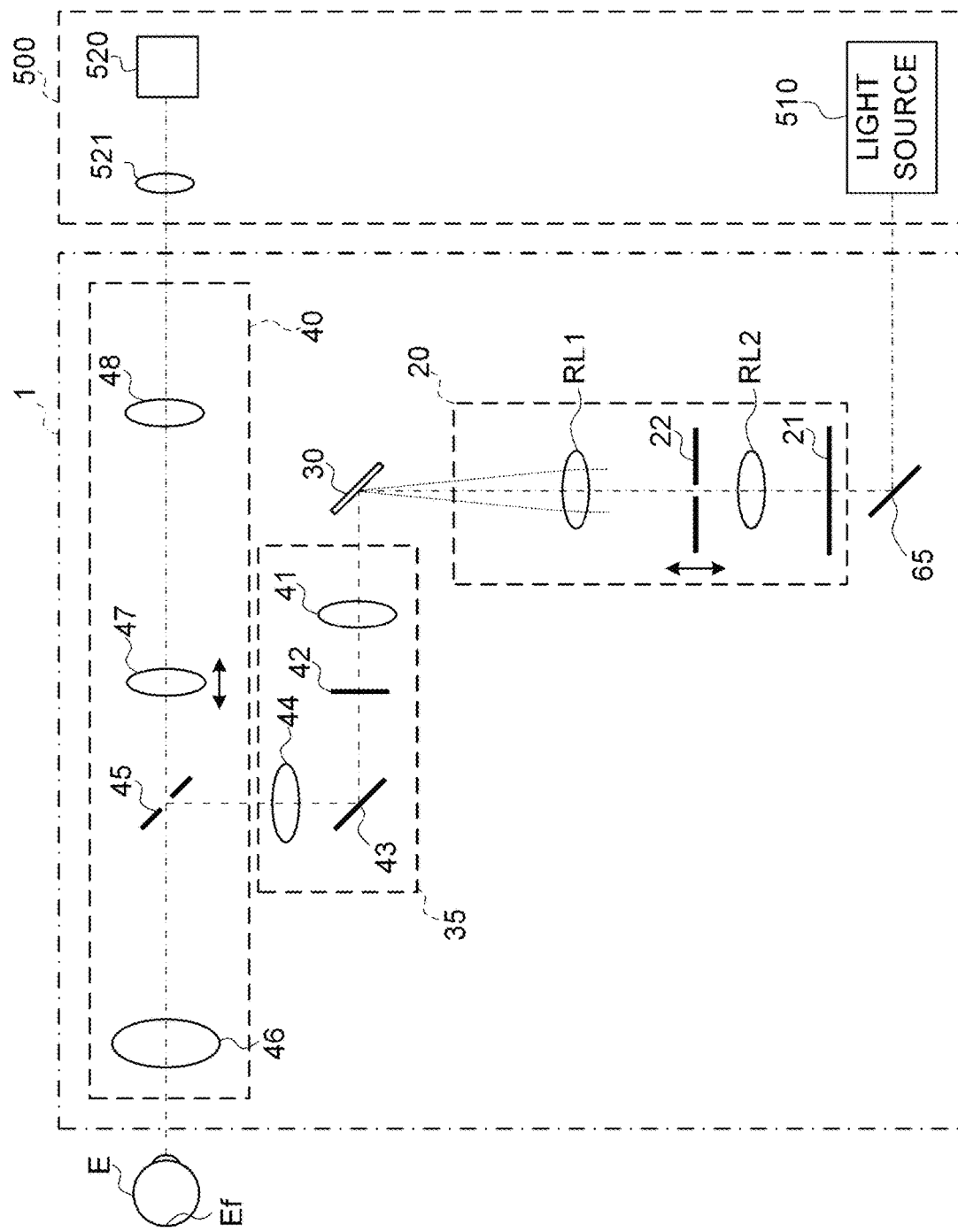

OPHTHALMIC APPARATUS AND OPHTHALMIC SYSTEM

CROSS-REFERENCE TO RELATED APPLICATIONS

The present application is a continuation application of International Patent Application No. PCT/JP2020/030484, filed Aug. 7, 2020, which claims priority to U.S. Provisional Application No. 62/898,961, filed Sep. 11, 2019. The contents of these applications are incorporated herein by reference in their entirety.

FIELD

The disclosure relates to an ophthalmic apparatus and an ophthalmic system.

BACKGROUND

In recent years, screening tests have been performed using ophthalmic apparatuses. Such ophthalmic apparatuses are expected to be applied to self-examinations, and further downsizing and weight saving of the ophthalmic apparatuses are desired. Various techniques have been proposed for this type of ophthalmic apparatus.

For example, U.S. Pat. No. 7,465,049 discloses a portable ophthalmic apparatus capable of easily acquiring an image of a subject's eye using a portable device having a function of imaging.

For example, U.S. Pat. No. 7,831,106 discloses an ophthalmic apparatus configured to pattern-illuminate a subject's eye using slit light and to detect returning light of the slit light using CMOS (Complementary Metal Oxide Semiconductor) image sensor. This ophthalmic apparatus can acquire high quality images of the subject's eye with a simple configuration without being affected by unnecessary light, by adjusting the illumination pattern and the timing of light reception using the CMOS image sensor.

SUMMARY

One aspect of some embodiments is an ophthalmic apparatus, including: an objective lens; an illumination optical system configured to generate illumination light using light from a light source, and to illuminate a subject's eye with the illumination light through the objective lens; a mounting unit configured to allow an external device including a sensor to be mounted so that the sensor is arranged on an imaging optical path; an imaging optical system configured to guide returning light of the illumination light from the subject's eye to the imaging optical path; a communication unit having a communication function with the external device; and a controller configured to control the illumination optical system and to control the sensor through the communication unit to synchronize with control for the illumination optical system.

Another aspect of some embodiments is an ophthalmic apparatus, including: an objective lens; an illumination optical system configured to generate illumination light using light from a light source, and to illuminate a subject's eye with the illumination light through the objective lens; a mounting unit configured to allow an external device including a sensor to be mounted so that the sensor is arranged on an imaging optical path; an imaging optical system configured to guide returning light of the illumination light from the subject's eye to the imaging optical path; a communication unit having a communication function with the external device; and a controller configured to control at least the illumination optical system, under control of the external device through the communication unit.

Yet another aspect of some embodiments is an ophthalmic system, including: the external device; and the ophthalmic apparatus of any one of the above.

BRIEF DESCRIPTION OF THE DRAWINGS

FIG. 4B is a schematic diagram for explaining an operation of the ophthalmic system according to the first embodiment.

FIG. 6 is a diagram illustrating an example of a configuration of an optical system of the ophthalmic apparatus according to the first embodiment.

DETAILED DESCRIPTION

Figure 1:
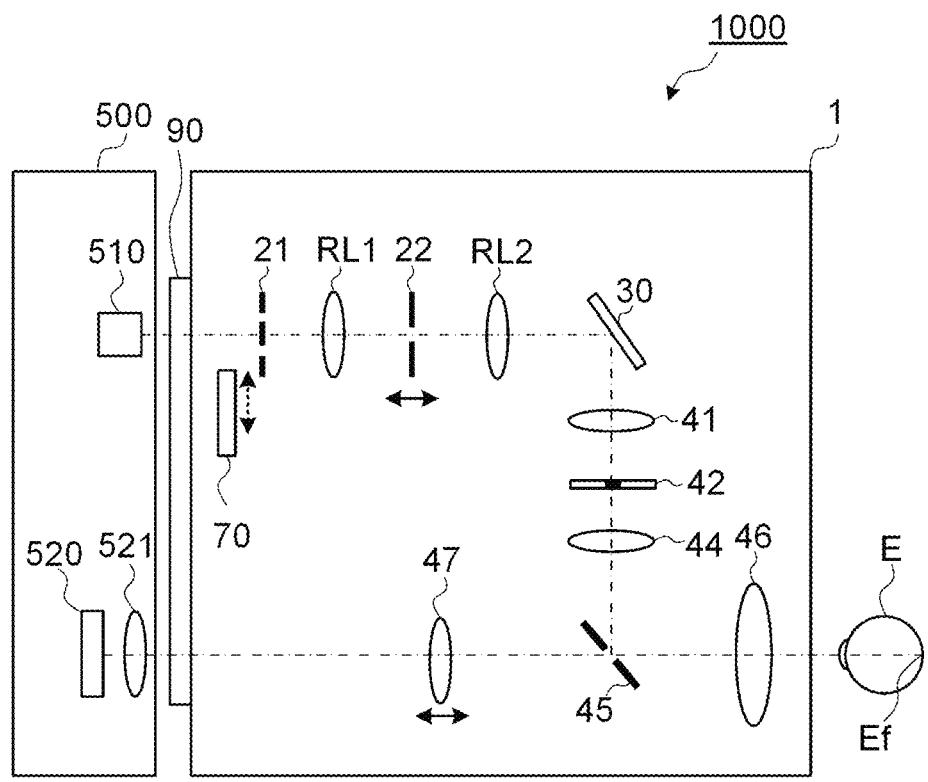
FIG. 1 is a schematic diagram illustrating an example of a configuration of an ophthalmic system according to a first embodiment.

For example, as disclosed in U.S. Pat. No. 7,465,049, the configuration of the ophthalmic apparatus can be simplified by measuring the subject's eye using the functions of an external device. In this case, for example, as disclosed in U.S. Pat. No. 7,831,106, the configuration of the ophthalmic apparatus can be further simplified by synchronously controlling the illumination side and the light receiving side (imaging side).

However, in the conventional method, the external device and the ophthalmic apparatus could not be controlled synchronously. As a result, further simplifying the configuration of the ophthalmic apparatus was limited.

According to some embodiments of the present invention, a new technique for observing a subject's eye with a simple configuration can be provided.

Referring now to the drawings, a detailed description is given of an example of an ophthalmic apparatus and an ophthalmic system according to the present invention. The contents of the document cited in the present specification can be appropriately incorporated as contents of the following embodiments.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

An ophthalmic system according to embodiments includes an external device and an ophthalmic apparatus. The ophthalmic apparatus can perform wired communication or wireless communication with the external device. In this specification, examples of the wired communication include communication according to predetermined communication standards such as the USB (Universal Serial Bus) standard, Ethernet (registered trademark) standard. Further, examples of the wireless communication include communication according to predetermined communication standards such as the wireless USB standard, wireless LAN (Local Area Network) according to predetermined communication standards such as the Wi-Fi (registered trademark) standard, WAN (Wide Area Network), communication according to near field wireless communication standards such as Bluetooth (registered trademark), communication using electromagnetic waves having a wavelength component within the wavelength range from the ultraviolet region to the radio wave region (including the visible region) such as infrared communication, optical communication, and radio wave communication, and communication using sound waves. It should be noted that the ophthalmic system according to the embodiments is not limited to the communication method between the external device and the ophthalmic apparatus.

The external device has at least an imaging function (light receiving function), in addition to the communication function. The ophthalmic apparatus is configured to project illumination light onto a subject's eye, the illumination light being generated using light from a light source, and to guide returning light of the illumination light from the subject's eye to the external device. In this case, the imaging (shooting) is performed by the external device in synchronization with the illumination pattern (movement timing of the illuminated position of the illumination light) irradiated by the ophthalmic apparatus, using the communication function between the external device and the ophthalmic apparatus.

In some embodiments, the external device has an illumination function (light source) and the imaging function, in addition to the communication function. In this case, the ophthalmic apparatus is configured to project illumination light onto the subject's eye, the illumination light being generated using light from a light source provided in the external device, and to guide returning light of the illumination light from the subject's eye to the external device.

For example, the ophthalmic apparatus irradiates a predetermined site of the subject's eye while moving the irradiated position (irradiated range) of the illumination light by deflecting the illumination light having a predetermined shape generated using the light from the light source. Alternatively, for example, the ophthalmic apparatus irradiates a predetermined site of the subject's eye while moving the irradiated position of the illumination light by performing light modulation on the illumination light generated using the light from the light source.

The ophthalmic apparatus guides the returning light of the illumination light from the subject's eye to the external device. The external device receives the returning light incident through the ophthalmic apparatus, using an image sensor. A result of light reception of the returning light is read out from light receiving element(s) at the light receiving position(s) of the returning light corresponding to the irradiated position(s) of the illumination light in synchronization with the movement timing of the irradiated position(s) of the illumination light (rolling shutter control).

In some embodiments, the ophthalmic apparatus performs synchronous control of the moving operation of the irradiated position of the illumination light and the light receiving operation of the image sensor in the external device. In some embodiments, the external device performs synchronous control of the moving operation of the irradiated position of the illumination light performed by the ophthalmic apparatus and the light receiving operation of the image sensor.

Such an external device may be any device having the imaging function and the communication function, or any device having the illumination function, imaging function, and the communication function. Examples of the external device include a mobile phone, a personal digital assistant (PDA), a digital camera, a tablet terminal, a personal computer, a projector with a camera, and a smartphone. Further, the external device may be a portable device.

In some embodiments, the predetermined site is an anterior segment or a posterior segment. Examples of the anterior segment include a cornea, an iris, a crystalline lens, a ciliary body, and a ciliary zonule. Examples of the posterior segment include a vitreous body, and a fundus or the vicinity of the fundus (retina, choroid, sclera, etc.).

A method of controlling the ophthalmic apparatus according to the embodiments includes one or more steps for realizing the processing executed by a processor (computer) in the ophthalmic apparatus according to the embodiments. A program according to the embodiments causes the processor to execute each step of the method of controlling the ophthalmic apparatus according to the embodiments.

Hereinafter, a case where the external device according to the embodiments is a smartphone and mainly acquires an image of the fundus of the subject's eye will be described. However, the configuration according to the embodiments can be applied to an ophthalmic system including an external device other than the smartphone. Further, the configuration according to the embodiments can be applied to an ophthalmic system that can acquire images other than the image of the fundus or can measure the site other than the fundus.

First Embodiment

FIG. 1 shows a block diagram of an example of a configuration of an ophthalmic system according to a first embodiment.

An ophthalmic system 1000 according to the first embodiment includes a smartphone 500 and an ophthalmic apparatus 1. The smartphone 500 has a communication function, an illumination function, and an imaging (shooting) function. The ophthalmic apparatus 1 relays illumination light generated using light from the smartphone 500 to a fundus Ef of a subject's eye E, and relays returning light of the illumination light from the fundus Ef to the smartphone 500. The smartphone 500 detects the returning light incident through the ophthalmic apparatus 1.

The smartphone 500 includes a light source 510, an image sensor 520, and an imaging lens 521.

In a housing of the smartphone 500, an outgoing opening (outgoing window) and an incoming opening (incoming window) are formed. Light from the light source 510 passes through the outgoing opening, and is emitted toward the outside of the housing. Light from the outside passing through the incoming opening passes through the imaging lens 521, and forms an image at the light receiving surface of the image sensor 520. In some embodiments, one or more lenses (optical elements) are provided in at least one of the outgoing opening and the incoming opening formed in the housing of the smartphone 500.

On the surface of the ophthalmic apparatus 1, a mounting unit 90 is provided for mounting (attaching) the smartphone 500. The mounting unit 90 is configured to be capable of holding the smartphone 500 by a known method. In this case, the mounting unit 90 is configured to allow an external device to be mounted so that the image sensor 520 is arranged on an imaging optical path (optical path of the imaging optical system 40 described below) and the light source 510 is arranged on an optical path of the illumination optical system of the ophthalmic apparatus 1. Examples of mode of mounting of the smartphone 500 to the ophthalmic apparatus 1 by the mounting unit 90 include fixing by screwing, fitting, or hanging, and crimping the smartphone 500 to the ophthalmic apparatus 1 using elastic force or magnetic force.

In some embodiments, the mounting unit 90 is configured to be capable of changing a relative position of the smartphone 500 to the optical system of the ophthalmic apparatus 1 while holding the ophthalmic apparatus 1. In some embodiments, the mounting unit 90 is configured to be capable of changing a relative position of the smartphone 500 to the optical system of the ophthalmic apparatus 1 in a direction of an optical axis of the light emitted from the light source 510 (optical axis of the light incident on the light receiving surface of the image sensor 520) while holding the ophthalmic apparatus 1.

In the mounting unit 90 (and the housing of the ophthalmic apparatus 1), an incoming opening and an incoming/outgoing opening (incoming/outgoing window), and an outgoing opening are formed. Light from the smartphone 500 passes through the incoming opening, and enters the inside of the housing. The ophthalmic apparatus 1 generates slit-shaped illumination light using light that passes through the incoming opening and enters the inside of the housing. The generated illumination light passes through the incoming/outgoing opening and is guided to the fundus Ef of the subject's eye E. Returning light of the illumination light from the fundus Ef passes through the incoming/outgoing opening and enters the inside of the housing. The returning light that enters the inside of the housing passes through the outgoing opening and is emitted toward the outside of the housing. In some embodiments, one or more lenses (optical elements) are provided in at least one the incoming opening, the incoming/outgoing opening, and the outgoing opening that are formed in the mounting unit 90.

The ophthalmic apparatus 1 has an optical system described below, as well as a communication function. The optical system of the ophthalmic apparatus 1 includes an iris aperture 21, a relay lens system RL1, a slit 22, a relay lens system RL2, an optical scanner 30, a relay lens 41, a black point plate 42, a relay lens 44, a perforated mirror 45, an objective lens 46, and a focusing lens 47.

In the iris aperture 21, one or more apertures are formed. The one or more apertures formed in the iris aperture 21 can be arranged (disposed) at a position substantially conjugate optically to an iris (pupil) of the subject's eye E. The iris aperture 21 is an optical element for pupil-dividing the illumination light and the returning light thereof.

In the slit 22, one or more slit-shaped apertures are formed. The one or more apertures formed in the slit 22 can be arranged at a position substantially conjugate optically to the fundus Ef which is an imaging site (measurement site) of the subject's eye E. The slit 22 can be moved along an optical axis. The slit 22 is an optical element for generating the slit-shaped illumination light.

The optical scanner 30 deflects the slit-shaped illumination light one-dimensionally or two-dimensionally. The optical scanner 30 (deflection surface of the optical scanner 30) can be arranged at a position substantially conjugate optically to the iris of the subject's eye E. In some embodiments, the optical scanner 30 deflects the slit-shaped illumination light in a one-dimensional direction corresponding to the shorter direction of the slit.

The black point plate 42 shields unnecessary reflected light going toward the light source side.

The perforated mirror 45 couples an optical path of the illumination light with an optical path of the returning light of the illumination light. In the perforated mirror 45, a hole is formed. The hole formed in the perforated mirror 45 can be arranged at a position substantially conjugate optically to the iris of the subject's eye E. The illumination light deflected by the optical scanner 30 is reflected toward the objective lens 46 on the peripheral region of the hole of the perforated mirror 45.

The illumination light reflected on the peripheral region of the hole formed in the perforated mirror 45 is refracted by the objective lens 46 and is irradiated onto the subject's eye E. The returning light of the illumination light from the subject's eye E passes through the objective lens 46, passes through the hole formed in the perforated mirror 45, and is guided to the focusing lens 47.

The focusing lens 47 can be moved along an optical axis. The returning light passing through the hole formed in the perforated mirror 45 passes through the focusing lens 47, and is guided to the smartphone 500.

In some embodiments, as shown in FIG. 1, a wavelength selective filter 70 is provided so as to be capable of inserting and removing from an optical path between the incoming opening and the iris aperture 21. The wavelength selective filter 70 is configured to be inserted and removed from the optical path using a known movement mechanism, manually or under control from the controller described below. The wavelength selective filter 70 passes light with wavelength component(s) corresponding to a predetermined wavelength selective characteristic among the wavelength components of the light from the smartphone 500. Examples of the wavelength component(s) selected by the wavelength selective filter 70 include wavelength component(s) within the wavelength range for fluorescein fluorescence imaging, wavelength component(s) within the wavelength range for indocyanine green fluorescence imaging, wavelength component(s) within the wavelength range for autofluorescence imaging, and wavelength component(s) within the wavelength range for imaging with light of any of the RGB color components.

In some embodiments, a condenser lens is arranged between the incoming opening and the iris aperture 21. In some embodiments, the objective lens 46 can be moved along an optical axis.

Figure 2:
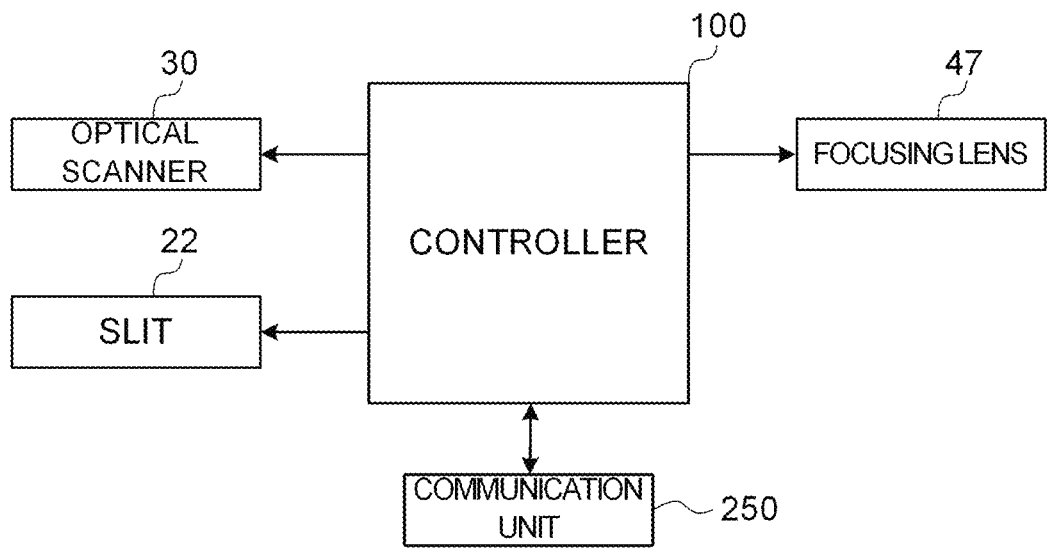
FIG. 2 is a schematic diagram illustrating an example of a configuration of a control system of an ophthalmic apparatus according to the first embodiment.

FIG. 2 shows a block diagram of an example of a control system in the ophthalmic apparatus 1 illustrated in FIG. 1. In FIG. 2, like reference numerals designate like parts as in FIG. 1. The same description may not be repeated.

As shown in FIG. 2, the control system of the ophthalmic apparatus 1 is configured with a controller 100 as a center. The controller 100 controls each part of the ophthalmic apparatus 1 that includes the slit 22, the optical scanner 30, the focusing lens 47, and a communication unit 250.

The controller 100 changes a position of the slit 22 on the optical axis by controlling the slit 22 (specifically, the movement mechanism that moves the slit 22). This allows to arrange the one or more apertures formed in the slit 22 at a position substantially conjugate optically to the fundus Ef, regardless of the state of the subject's eye E such as the refractive power and the axial length.

The controller 100 performs the deflection control for the illumination light by controlling the optical scanner 30. This allows to control the irradiated position of the illumination light on the fundus Ef and the movement timing of the irradiated position.

The controller 100 changes a position of the focusing lens 47 on the optical axis by controlling the focusing lens 47 (specifically, the movement mechanism that moves the focusing lens 47). This allows to image the returning light on the light receiving surface of the image sensor 520, regardless of the state of the subject's eye E.

The communication unit 250 performs the communication processing with the smartphone 500 in accordance with a predetermined communication standard. The controller 100 can transmit communication signal(s) to the smartphone 500 by controlling the communication unit 250 and can perform the control corresponding to the communication signal(s) for the smartphone 500. In some embodiments, the controller 100 can receive communication signal(s) from the smartphone 500 by controlling the communication unit 250 and can perform the control corresponding to the communication signal(s) for each part of the ophthalmic apparatus 1.

The function of the controller 100 is realized by a processor. That is, the controller 100 reads a program stored in a storage unit (not shown), and executes it to perform processing corresponding to the program, thereby, implementing the functions of the controller 100.

Figure 3:
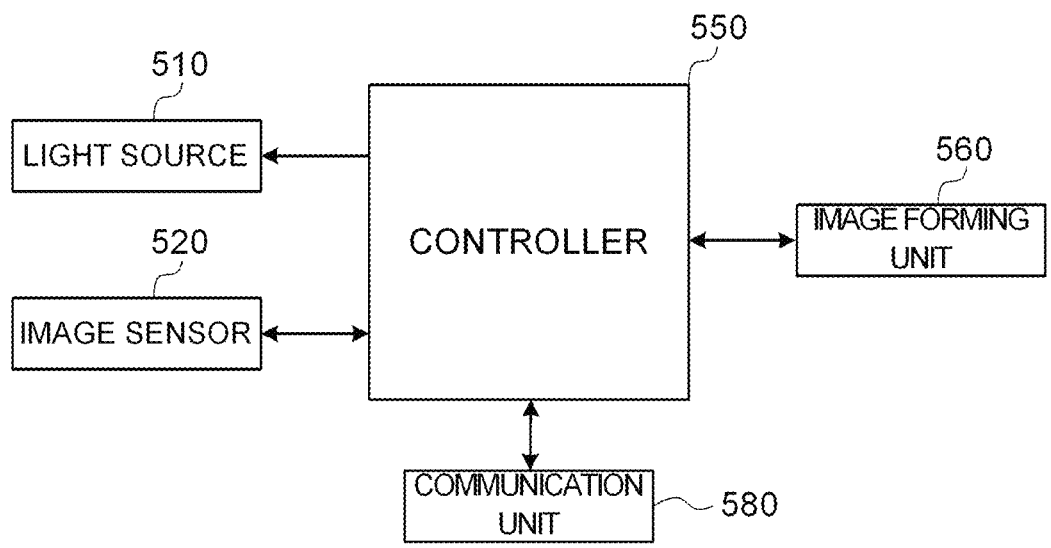
FIG. 3 is a schematic diagram illustrating an example of a configuration of a control system of a smartphone according to the first embodiment.

FIG. 3 shows a block diagram of an example of a control system in the smartphone 500 illustrated in FIG. 1. In FIG. 3, like reference numerals designate like parts as in FIG. 1, and the redundant explanation may be omitted as appropriate.

As shown in FIG. 3, the control system of the smartphone 500 is configured with a controller 550 as a center. The controller 550 controls each part of the smartphone 500 that includes a light source 510, the image sensor 520, an image forming unit 560, and a communication unit 580.

Examples of the control for the light source 510 include switching on/off the light source 510, and changing of the amount of light. In some embodiments, the controller 550 controls at least one of a position of the light source 510 and an orientation of an emission direction of the emitted light. In some embodiments, the controller 550 controls the switching of the center wavelength of the light emitted by the light source 510.

Examples of the control for the image sensor 520 include control of light reception of the returning light using rolling shutter method, control of light reception rate, and control of light reception sensitivity.

The image forming unit 560 forms an image of the subject's eye E (fundus Ef) based on a result of light reception of the returning light acquired using the image sensor 520. For example, the image forming unit 560 forms the image of the fundus Ef based on a detection result of the returning light and the pixel position signal. The pixel position signal is generated from irradiated position information of the illumination light on the fundus Ef and position information of the light receiving element that received the returning light in the image sensor 520, for example. The irradiated position information can be specified from deflection control information of the optical scanner 30, for example.

The communication unit 580 performs the communication processing with the ophthalmic apparatus 1 in accordance with the same communication standards as the communication processing performed by the communication unit 250. The controller 550 can receive communication signal(s) from the ophthalmic apparatus 1 by controlling the communication unit 580 and can perform the control corresponding to the communication signal(s) for each part of the smartphone 500. In some embodiments, the controller 550 can transmit communication signal(s) to the ophthalmic apparatus 1 by controlling the communication unit 580 and can perform the control corresponding to the communication signal(s) for each part of the ophthalmic apparatus 1.

The function of the controller 550 is realized by a processor. That is, the controller 550 reads a program stored in a storage unit (not shown), and executes it to perform processing corresponding to the program, thereby, implementing the functions of the controller 550.

Figure 4A:
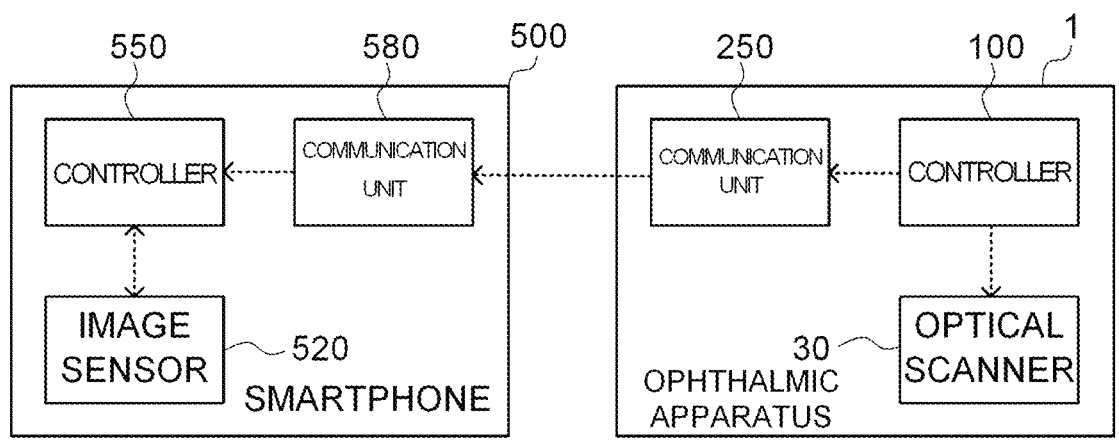
FIG. 4A is a schematic diagram for explaining an operation of the ophthalmic system according to the first embodiment.

FIGS. 4A and 4B show diagrams describing a first operation example of the ophthalmic system 1000 according to the first embodiment. FIG. 4A schematically represents the flow of the control of the ophthalmic system 1000. In FIG. 4A, like reference numerals designate like parts as in FIG. 2 or FIG. 3. The same description may not be repeated. FIG.

4B represents an example of the control sequence in each part of the ophthalmic system 1000.

In the first operation example, the ophthalmic apparatus 1 controls the smartphone 500 to acquire images of the fundus Ef using the rolling shutter method.

First, communication connection is established between the ophthalmic apparatus 1 and the smartphone 500, using a known method (SQ1). For example, the controller 100 controls the communication unit 250 to establish the communication connection between the communication unit 250 and the communication unit 580 in the smartphone 500. In the same manner, the controller 550 controls the communication unit 580 to establish the communication connection between the communication unit 580 and the communication unit 250 in the ophthalmic apparatus 1.

When the photographing of the fundus Ef of the subject's eye E is started, the controller 100 controls the communication unit 250 to transmit communication signal(s) for synchronizing the movement control of the irradiated position of the illumination light and the light reception control using the image sensor 520 (SQ2).

Subsequently, the controller 100 controls the optical scanner 30 to deflect the deflection angle of the illumination light by a predetermined step (SQ3). In contrast, the controller 550 in the smartphone 500 controls the communication unit 580 to receive communication signal(s) from the ophthalmic apparatus 1, and controls the image sensor 520 in response to the received communication signal(s) to perform light reception control of the returning light on the image sensor 520 in synchronization with the deflection control for the optical scanner 30 (SQ4).

Thereafter, after a predetermined time has elapsed, the controller 100 controls the communication unit 250 to transmit communication signal(s) to the smartphone 500 in the same manner as in SQ2 (SQ5). Subsequently, the controller 100 controls the optical scanner 30 to perform the deflection control of the illumination light, in the same manner as in SQ3 (SQ6). The controller 550 in the smartphone 500 receives the communication signal(s) from the ophthalmic apparatus 1, and performs the light reception control of the returning light on the image sensor 520 in synchronization with the deflection control for the optical scanner 30 in response to the received communication signal(s), in the same manner as in SQ4 (SQ7).

Thereafter, the transmission of the communication signal(s) performed by the controller 100 (SQ8), the deflection control performed by the controller 100 (SQ9), and the light reception control performed by the controller 550 (SQ10) are repeated sequentially.

In some embodiments, after the transmission of the communication signal(s) is performed by the controller 100, the deflection control performed by the controller 100 and the light reception control performed by the controller 550 are repeated a plurality of times.

Figure 5A:
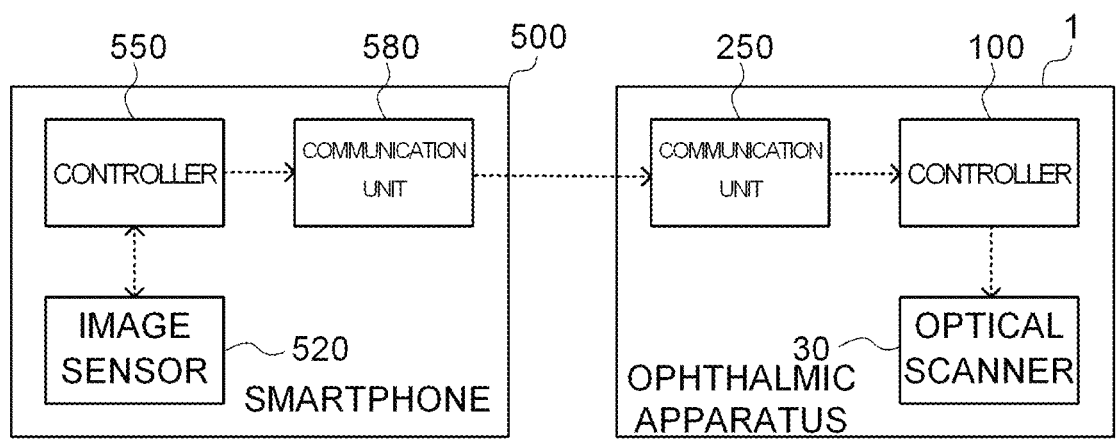
FIG. 5A is a schematic diagram for explaining an operation of the ophthalmic system according to the first embodiment.
Figure 5B:
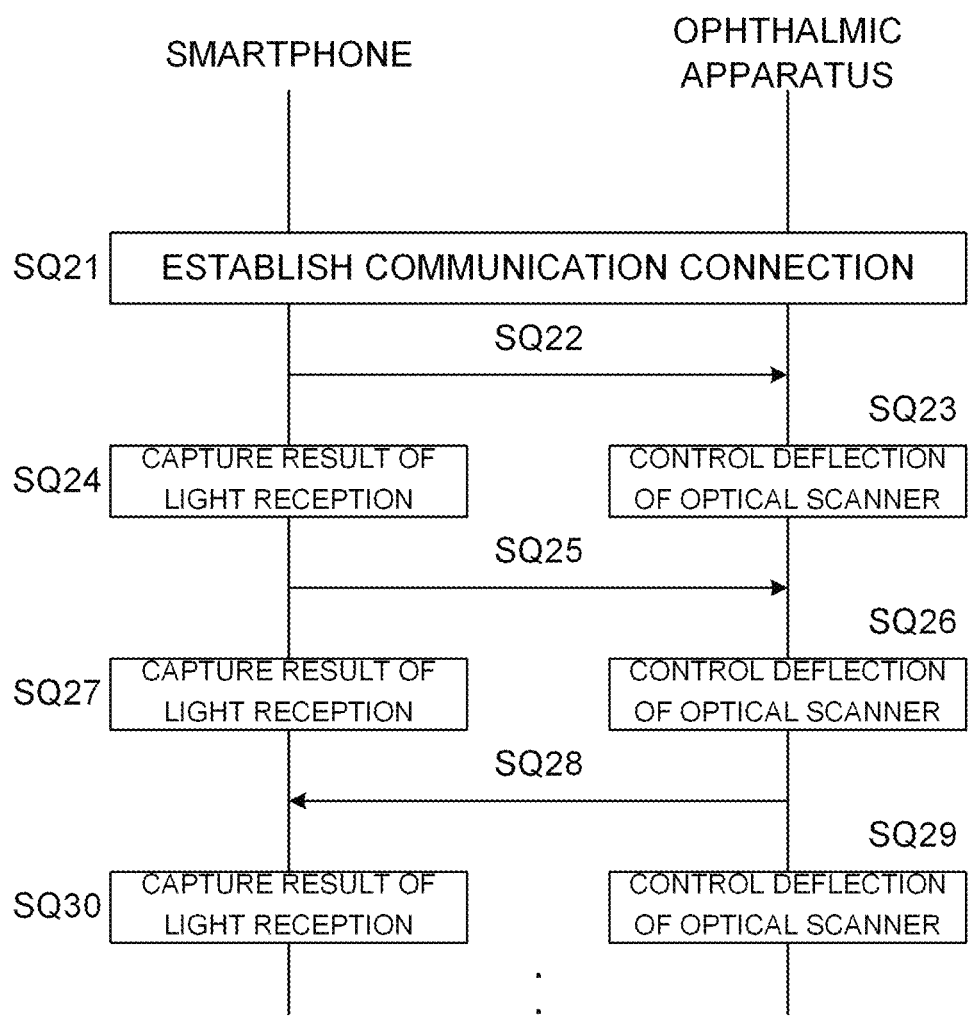
FIG. 5B is a schematic diagram for explaining an operation of the ophthalmic system according to the first embodiment.

FIGS. 5A and 5B show diagrams describing a second operation example of the ophthalmic system 1000 according to the first embodiment. FIG. 5A schematically represents the flow of the control of the ophthalmic system 1000. In FIG. 5A, like reference numerals designate like parts as in FIG. 2 or FIG. 3. The same description may not be repeated. FIG. 5B represents an example of the control sequence in each part of the ophthalmic system 1000.

In the second operation example, the smartphone 500 controls the ophthalmic apparatus 1 to acquire images of the fundus Ef using the rolling shutter method.

First, communication connection is established between the ophthalmic apparatus 1 and the smartphone 500, using a known method (SQ21). For example, the controller 550 controls the communication unit 580 to establish the communication connection between the communication unit 580 and the communication unit 250 in the ophthalmic apparatus 1. In the same manner, the controller 100 controls the communication unit 250 to establish the communication connection between the communication unit 250 and the communication unit 580 in the smartphone 500.

When the photographing of the fundus Ef of the subject's eye E is started, the controller 550 controls the communication unit 580 to transmit communication signal(s) to the ophthalmic apparatus 1 (SQ22). Here, the communication signal(s) is/are signal(s) for synchronizing the movement control of the irradiated position of the illumination light and the light reception control using the image sensor 520.

Subsequently, the controller 100 in the ophthalmic apparatus 1 controls the communication unit 250 to receive the communication signal(s) from the smartphone 500, and performs the deflection control for the optical scanner 30 in response to the received communication signal(s) (SQ23). The controller 550 controls the image sensor 520 to perform the light reception control of the returning light on the image sensor 520 in synchronization with the deflection control for the optical scanner 30 (SQ24).

In the same manner as the first operation example, thereafter, the transmission of communication signal(s) performed by the controller 550 (SQ25), the deflection control performed by the controller 100 (SQ26), and the light reception control performed by the controller 550 (SQ27) are repeated sequentially (SQ28 to SQ30).

In some embodiments, after the transmission of the communication signal(s) is performed by the controller 550, the deflection control performed by the controller 100 and the light reception control performed by the controller 550 are repeated a plurality of times.

In the following, the ophthalmic system 1000 that performs the above first operation example will be described in detail.

[Configuration of Optical System of Ophthalmic Apparatus 1]

Figure 7:
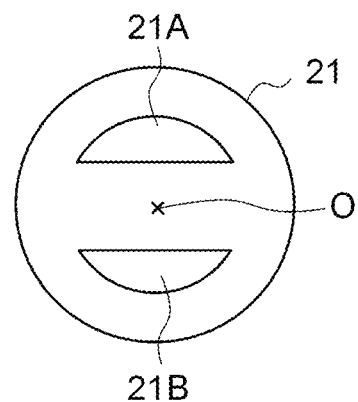
FIG. 7 is a diagram illustrating an example of a configuration of an optical system of the ophthalmic apparatus according to the first embodiment.
Figure 8:
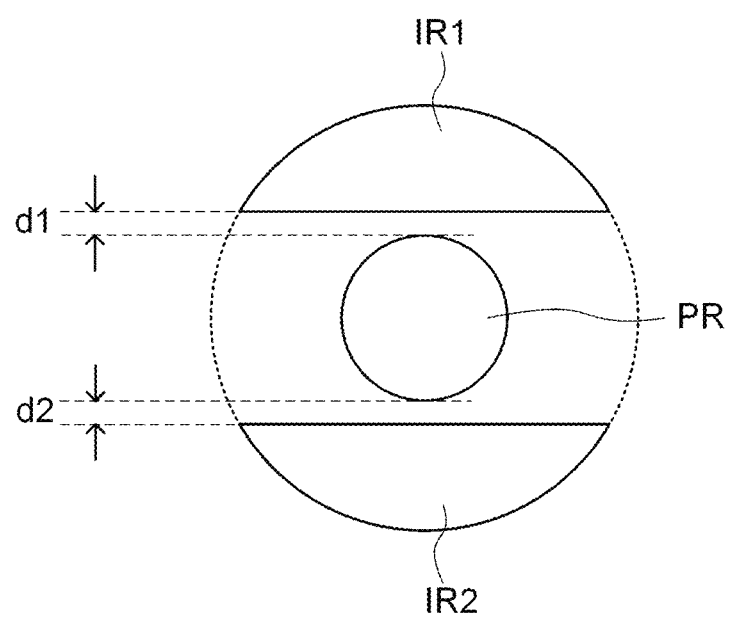
FIG. 8 is a diagram illustrating an example of a configuration of an optical system of the ophthalmic apparatus according to the first embodiment.
Figure 9:
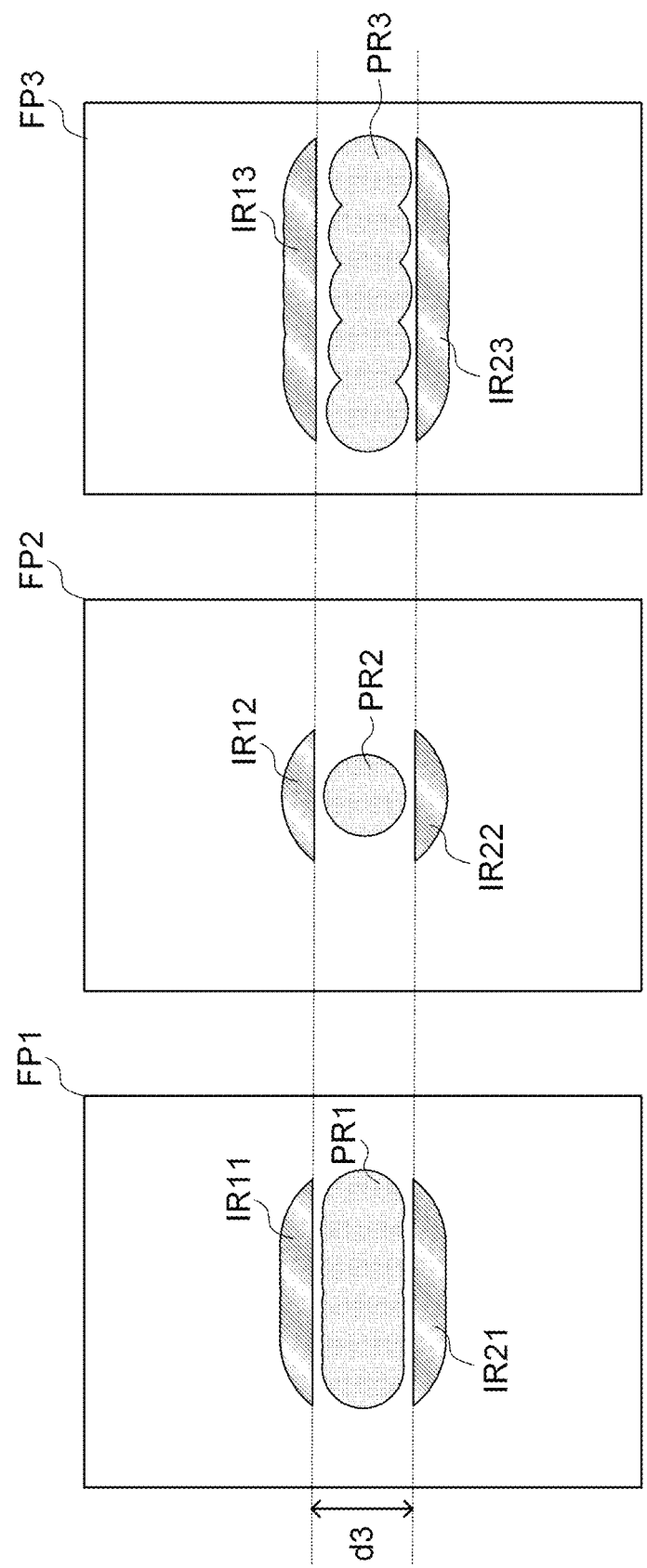
FIG. 9 is an explanatory diagram of an operation of the ophthalmic apparatus according to the first embodiment.
Figure 10:
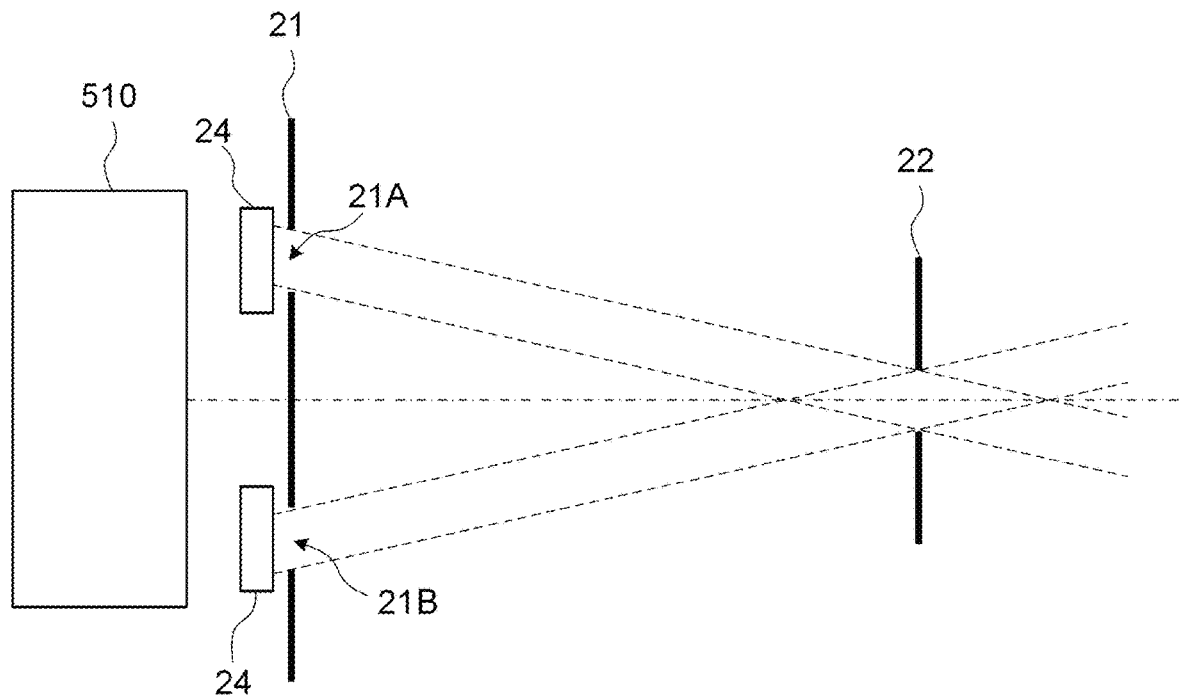
FIG. 10 is an explanatory diagram of an operation of the ophthalmic apparatus according to the first embodiment.
Figure 11:
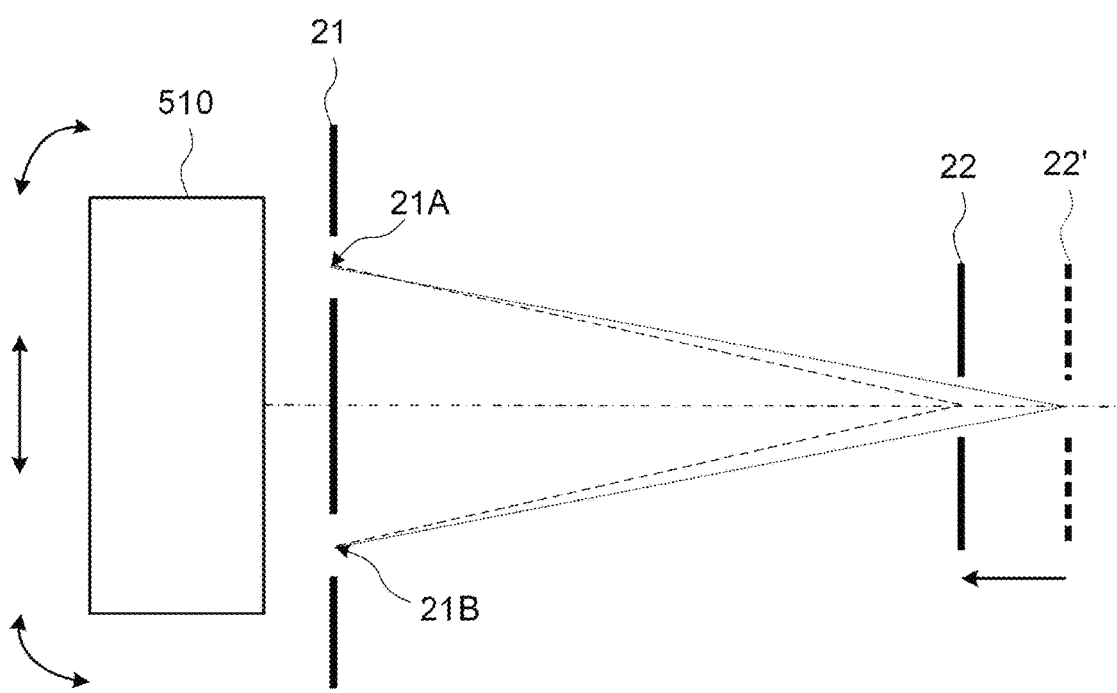
FIG. 11 is an explanatory diagram of an operation of the ophthalmic apparatus according to the first embodiment.
Figure 12:
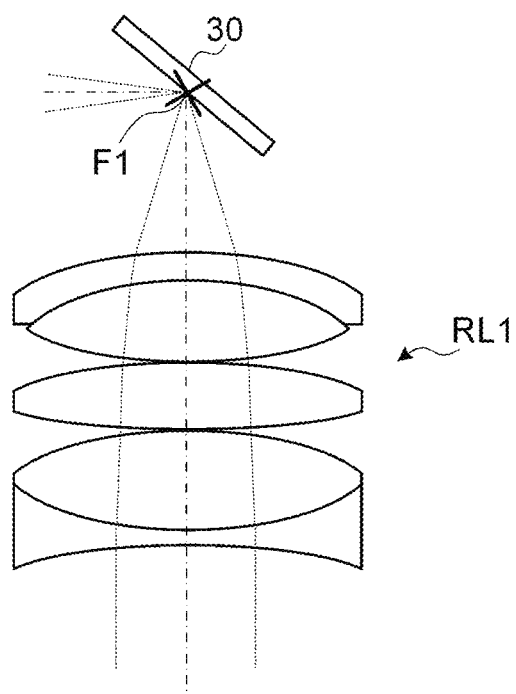
FIG. 12 is a diagram illustrating an example of a configuration of an optical system of the ophthalmic apparatus according to the first embodiment.
Figure 13:
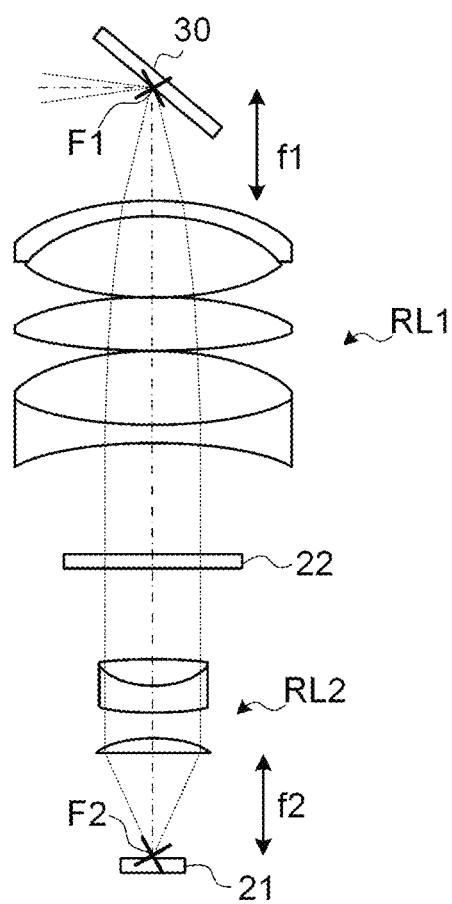
FIG. 13 is a diagram illustrating an example of a configuration of an optical system of the ophthalmic apparatus according to the first embodiment.

FIGS. 6 to 13 show examples of the configuration of an optical system of the ophthalmic apparatus 1 that constitutes the ophthalmic system 1000 according to the first embodiment. In FIG. 6, the smartphone 500 that constitutes the ophthalmic system 1000 is shown in the figures. FIG. 7 schematically represents an example of the configuration of the iris aperture 21 in FIG. 6 when viewed from a direction of an optical axis O. FIG. 8 schematically represents a shape of luminous flux cross section of the illumination light. FIG. 9 represents a diagram describing the iris aperture 21 in FIG. 6. FIG. 10 represents an example of the configuration of the iris aperture 21 in FIG. 6 and the slit 22 in FIG. 6 when viewed from the side or top. FIG. 11 represents a diagram describing a light source 510 in FIG. 6. FIG. 12 represents an example of the configuration of a relay lens system RL1 in FIG. 6. FIG. 13 represents an example of the configuration of a relay lens system RL2 in FIG. 6. In FIGS. 12 and 13, the case where the relay lens system RL1 includes three lenses is shown, however the number of lenses that make up the relay lens system RL1 is not limited. Further, in FIG. 13, the case where the relay lens system RL2 includes two lenses is shown, however the number of lenses that make up the relay lens system RL2 is not limited. In FIGS. 6 to 13, like parts are designated by like reference numerals as in FIG. 1 and repetitious description of such parts may not be provided.

First, the ophthalmic apparatus 1 will be described.

The ophthalmic apparatus 1 includes an illumination optical system 20, the optical scanner 30, a projection optical system 35, and an imaging optical system 40. In some embodiments, the illumination optical system 20 includes at least one of the optical scanner 30 and the projection optical system 35.

Light emitted from the light source 510 in the smartphone 500 passes through the incoming opening formed in the mounting unit 90 of the ophthalmic apparatus 1, and is reflected by a mirror 65 toward the illumination optical system 20.

(Illumination Optical System 20)

The illumination optical system 20 generates the slit-shaped illumination light using the light from the light source 510 reflected by the mirror 65. The illumination optical system 20 guides the generated illumination light to the optical scanner 30.

The illumination optical system 20 includes the iris aperture 21, the slit 22, and the relay lens systems RL1 and RL2. The relay lens system RL1 is arranged between the optical scanner 30 and the slit 22. The relay lens system RL2 is arranged between the iris aperture 21 and the slit 22.

As described above, the iris aperture 21 (specifically, aperture(s) of the iris aperture 21) can be arranged at a position substantially conjugate optically to the iris (pupil) of the subject's eye E. In the iris aperture 21, one or more apertures are formed at positions away from the optical axis O.

The relay lens system RL2 includes one or more lenses, and guides the illumination light passing through the aperture formed in the iris aperture 21 to the slit 22.

As described above, the slit 22 (specifically, aperture(s) of the slit 22) can be arranged at a position substantially conjugate optically to the fundus Ef of the subject's eye E. For example, in the slit 22, the aperture is formed in a direction corresponding to a line direction (row direction) that is read out from the image sensor 520 using the rolling shutter method.

The relay lens system RL1 includes one or more lenses, and guides the illumination light passing through the aperture formed in the slit 22 to optical scanner 30.

As described above, in the illumination optical system 20, the light from the light source 510 passing through the incoming opening passes through the aperture(s) formed in the iris aperture 21, is transmitted through the relay lens system RL2, passes through the aperture formed in the slit 22 to become slit-shaped illumination light, and is transmitted through the relay lens system RL1. The light transmitted through the relay lens system RL1 is guided to the optical scanner 30.

(Optical Scanner 30)

The optical scanner 30 is disposed at a position substantially conjugate optically to the iris of the subject's eye E, as described above. The optical scanner 30 deflects the illumination light passing through the relay lens system RL1. Specifically, the optical scanner 30 deflects the slit-shaped illumination light for sequentially illuminating a predetermined irradiated region of the fundus Ef to guide the illumination light to the projection optical system 35, while changing the deflection angle within a predetermined deflection angle range with the iris or the vicinity of the iris of the subject's eye E as a scan center position. The optical scanner 30 can deflect the illuminating light one-dimensionally or two-dimensionally.

In case that the optical scanner 30 deflects the illumination light one-dimensionally, the optical scanner 30 includes a galvano scanner that deflects the illuminating light within a predetermined deflection angle range with reference to a predetermined deflection direction. In case that the optical scanner 30 deflects the illumination light two-dimensionally, the optical scanner 30 includes a first galvano scanner and a second galvano scanner. The first galvano scanner deflects the illumination light so as to move the irradiated position of the illumination light in a horizontal direction orthogonal to the optical axis of the imaging optical system 40 (illumination optical system 20). The second galvano scanner deflects the illuminating light deflected by the first galvano scanner so as to move the irradiated position of the illumination light in a vertical direction orthogonal to the optical axis of the imaging optical system 40 (illumination optical system 20). Examples of scan mode for moving the irradiated position of the illumination light using the optical scanner 30 include a horizontal scan, a vertical scan, a cross scan, a radial scan, a circle scan, a concentric scan, and a helical (spiral) scan.

(Projection Optical System 35)

The projection optical system 35 guides the illumination light deflected by the optical scanner 30 to the perforated mirror 45.

The projection optical system 35 includes the relay lens 41, the black point plate 42, the reflective mirror 43, and the relay lens 44. Each of the relay lenses 41 and 44 includes one or more lenses.

(Black Point Plate 42)

The black point plate 42 is arranged at a position substantially conjugate optically to a lens surface of the objective lens 46 or the vicinity of the lens surface of the objective lens 46. This allows to prevent reflected light from the lens surface of the objective lens 46 from being guided to the light source 510 (smartphone 500).

In the projection optical system 35 with this configuration, the illumination light deflected by the optical scanner 30 is transmitted through the relay lens 41, passes through the black point plate 42, is reflected by the reflective mirror 43, is transmitted through the relay lens 44, and is guided to the perforated mirror 45.

(Imaging Optical System 40)

The imaging optical system 40 guides the illumination light that has been guided through the projection optical system 35 to the fundus Ef of the subject's eye E, and also guides the returning light of the illumination light from the fundus Ef to the smartphone 500 (image sensor 520).

In the imaging optical system 40, an optical path of the illumination light from the projection optical system 35 and an optical path of the returning light of the illumination light from the fundus Ef are coupled. By using the perforated mirror 45 as an optical path coupling member to couple these optical paths, it enables pupil division between the illumination light and the returning light of the illumination light.

The imaging optical system 40 includes the perforated mirror 45, the objective lens 46, the focusing lens 47, and an relay lens 48. The relay lens 48 includes one or more lenses.

In the perforated mirror 45, the hole is formed as described above. The hole is arranged on the optical axis of the imaging optical system 40. The hole of the perforated mirror 45 is arranged at a position substantially conjugate optically to the iris of the subject's eye E, as described above. The perforated mirror 45 reflects the illumination light from the projection optical system 35 toward the objective lens 46, on the peripheral region of the hole. The perforated mirror 45 like this functions as a photographic stop.

That is, the perforated mirror 45 is configured to combine the optical path of the illumination optical system 20 (projection optical system 35) and the optical path of the imaging optical system 40 arranged in a direction of the optical axis passing through the hole, and also to guide the illumination light reflected on the peripheral region of the hole to the fundus Ef.

The focusing lens 47 can be moved in an optical axis direction of the imaging optical system 40 using a movement mechanism (not shown). The movement mechanism moves the focusing lens 47 in the optical axis direction under the control from the controller 100. This allows to image the returning light of the illumination light passing through the hole of the perforated mirror 45 on the light receiving surface of the image sensor 520 in accordance with the state of the subject's eye E.

In the imaging optical system 40 with this configuration, the illumination light from the projection optical system 35 is reflected toward the objective lens 46 on the peripheral region formed in the perforated mirror 45. The illumination light reflected on the peripheral region of perforated mirror 45 is refracted by the objective lens 46, enters into the eye through the pupil of the subject's eye E, and illuminates the fundus Ef of the subject's eye E.

The returning light of the illumination light from the fundus Ef is refracted by the objective lens 46, passes through the hole of the perforated mirror 45, is transmitted through the focusing lens 47, is transmitted through the relay lens 48, is guided to the imaging lens 521 in the smartphone 500 through the outgoing opening.

Hereinafter, each part of the ophthalmic apparatus 1 according to the embodiments will be described.
(Iris Aperture 21)

First, the iris aperture 21 will be described. In the iris aperture 21, the aperture that defines an incident position (incident shape) of the illumination light on the iris of the subject's eye E is formed.

For example, by forming the apertures in the iris aperture 21 as shown in FIG. 7, the illumination light can enter into the eye from positions deviated from the pupil center (specifically, point-symmetrical positions centered on the pupil center) when the pupil center of the subject's eye E is arranged on the optical axis O.

In the iris aperture 21, one or more apertures are formed so that a luminous flux cross section of the illumination light (illumination luminous flux cross section) and a luminous flux cross section of returning light from the subject's eye E (fundus Ef) (imaging luminous flux cross section) are separated on a reflective site in the path of the illumination light in the subject's eye E. The shape of the aperture(s) formed in the iris aperture is not limited, as long as the illumination luminous flux cross section and the imaging luminous flux cross section are separated at the reflective site described above. Examples of the reflective site include a cornea (anterior surface of cornea, posterior surface of cornea), an anterior surface of lens, and a posterior surface of lens.

For example, apertures 21A and 21B are formed in the iris aperture 21, as shown in FIG. 7. The apertures 21A and 21B are formed line-symmetrically with respect to a straight line extending through the position of the optical axis O in a direction corresponding to a longitudinal direction of the slit 22.

Each of the apertures 21A and 21B has a circular segment shape. The circular segment is the region bounded by the inferior arc of a circle or ellipse and the chord of this inferior arc. A direction of the chord of the circular segment shape is approximately parallel to a direction corresponding to the longitudinal direction of the aperture(s) formed in slit 22.

In case of illuminating the subject's eye E using the iris aperture 21, the luminous flux cross section is formed on the pupil of the subject's eye E as shown in FIG. 8, for example.

In FIG. 8, light passing through the apertures 21A and 21B formed in the iris aperture 21 enters into the eye so as to form the luminous flux cross sections IR1 and IR2 on the pupil, for example. The luminous flux cross section IR1 is a luminous flux cross section of the light passing through the aperture 21A, for example. The luminous flux cross section IR2 is a luminous flux cross section of the light passing through the aperture 21B, for example.

The returning light (imaging light) that enters into the eye and is reflected on the fundus Ef forms the luminous flux cross section PR on the pupil, for example, and is guided to the imaging optical system 40.

In this case, the apertures 21A and 21B are formed so as to separate the luminous flux cross sections IR1 and IR2 of the illumination light and the luminous flux cross section PR of the imaging light.

The illumination luminous flux cross section and the imaging luminous flux cross section at each part of the eye of the subject's eye are formed as shown in FIG. 9. FIG. 9 schematically represents footprints PF1 to PF3 when the optical scanner 30 deflects with a predetermined deflection angle. The footprint FP1 represents the luminous flux cross section on the surface of the cornea. The footprint FP2 represents the luminous flux cross section on the anterior surface of lens (surface of the iris) (or surface of the photographic stop). The footprint FP3 represents the luminous flux cross section on the posterior surface of lens.

The anterior surface of lens (iris surface) (or surface of the photographic stop) is arranged at a position substantially conjugate optically to the iris aperture 21. Thereby, as shown in the footprint FP2, the same illumination luminous flux cross sections IR12 and IR22 and the imaging luminous flux cross section PR 2 as in FIG. 9 are formed. The respective shapes of the illumination luminous flux cross sections IR12 and IR22 are almost the same as the respective shapes of the apertures 21A and 21B formed in the iris aperture 21. The shape of the imaging luminous flux cross section PR2 is almost the same as the shape of the photographic stop (aperture formed in the perforated mirror 45). At the position, which is substantially conjugate optically to the iris aperture 21, the illumination luminous flux cross section and the imaging luminous flux cross section are separated, as in the footprint FP2.

On the corneal surface, which is non-conjugate optically to the iris aperture 21, the illumination luminous flux cross sections IR11 and IR21 and the imaging luminous flux cross section PR1 spread in the direction corresponding to the longitudinal direction of the slit 22 (footprint FP1). Meanwhile, the relative relationship between the illumination luminous flux cross sections IR11 and IR21 and the imaging luminous flux section PR1 in the direction corresponding to the shorter direction of the slit 22 does not change.

In the same way, on the posterior surface of lens, which is non-conjugate optically to the iris aperture 21, the illumination luminous flux cross sections IR13 and IR23 and the imaging luminous flux cross section PR3 spread in the direction corresponding to the longitudinal direction of the slit 22 (footprint FP3). Meanwhile, the relative relationship between the illumination luminous flux cross sections IR13 and IR23 and the imaging luminous flux cross section PR3 in the direction corresponding to the shorter direction of the slit 22 does not change.

At the position, which is non-conjugate optically to the iris aperture 21, when the deflection angle of the illumination light is changed by the optical scanner 30, the positions of the illumination luminous flux cross section and the imaging luminous flux cross section move in the direction corresponding to the shorter direction of the slit 22. Even if the deflection angle changes, the relative relationship between the illumination luminous flux cross section and the imaging luminous flux cross section as shown in footprints FP1 and FP3 is maintained.

Therefore, the aperture 21A formed in the iris aperture 21 is required to be formed so that the distance d1 (distance in the direction corresponding to the shorter direction of the slit 22) between the lower end of the illumination luminous flux cross section (luminous flux cross section IR1) and the upper end of the imaging luminous flux cross section (luminous flux cross section PR) is greater than or equal to a predetermined first distance, as shown in FIG. 8. In the same way, the aperture 21B formed in the iris aperture 21 is required to be formed so that the distance d2 between the upper end of the illumination luminous flux cross section (luminous flux cross section IR2) and the lower end of the imaging luminous flux cross section (luminous flux cross section PR) is greater than or equal to a predetermined second distance, as shown in FIG. 8. Here, the first distance may be equal to the second distance. Further, the apertures 21A and 21B formed in the iris aperture 21 are required to be formed so that the distance d3 in the direction corresponding to the shorter direction of the slit 22 is greater than or equal to a predetermined third distance, as shown in FIG. 9.

That is, the shapes of the inner diameters of the apertures 21A and 21B does not contribute to the shapes of the illumination luminous flux cross section and the shape of the imaging luminous flux cross section.

As described above, the apertures 21A and 21B are formed in the iris aperture 21 so that the illumination luminous flux cross section and the imaging luminous flux cross section are separated at the cornea, the anterior surface of lens, and the posterior surface of lens of the subject's eye E. Thereby, without being affected by unnecessary scattered light, high quality images of the fundus Ef with strong contrast can be acquired using a simple configuration.

In particular, by shaping the apertures 21A and 21B as shown in FIG. 7, the light amount of the illumination light can be increased, making it possible to acquire images with higher image quality.

In some embodiments, the ophthalmic apparatus 1 includes an optical element 24 arranged between the light source 510 (the incoming opening formed in the mounting unit 90 of the ophthalmic apparatus 1) and the iris aperture 21, as shown in FIG. 10. The optical element 24 can be arranged at a position substantially conjugate optically to the iris of the subject's eye E. The optical element 24 deflects the light from the light source 510 passing through the incoming opening. The optical element 24 deflects the illumination light so that the light amount distribution in a direction connecting the aperture 21A (or aperture 21B) formed in the iris aperture 21 and the aperture formed in the slit 22 is maximized. Examples of such optical element include a prism, a microlens array, or a Fresnel lens. In FIG. 10, the optical element 24 is provided for each aperture formed in the iris aperture 21. However, a single element may be configured to deflect the light passing through the apertures 21A and 21B in the iris aperture 21.

Further, the light amount distribution of the light passing through the aperture formed in the iris aperture 21 can be changed by changing a relative position between the light source 510 (or incoming opening formed in the mounting unit 90 of the ophthalmic apparatus 1) and the aperture formed in the iris aperture 21.

(Slit 22)

Next, the slit 22 will be described. In the slit 22, the aperture that defines an illumination pattern of the illumination light on the fundus Ef of the subject's eye E is formed.

The slit 22 can be moved in the optical axis direction of the illumination optical system 20 using a movement mechanism (movement mechanism 22D described below). The movement mechanism moves the slit 22 in the optical axis direction under the control from the controller 100. For example, the controller 100 controls the movement mechanism in accordance with the state of the subject's eye E. This allows to move the position of the slit 22 in accordance with the state of the subject's eye E (specifically, the refractive power or the shape of the fundus Ef).

In some embodiments, the slit 22 is configured so that at least one of the position of the aperture and the shape of the aperture can be changed in accordance with the state of the subject's eye E without being moved in the optical axis direction. The function of the slit 22 like this is realized, for example, by a liquid crystal shutter.

(Relay Lens System RL1)

In FIG. 6, the optical system is configured according to Badal's principle. Specifically, the relay lens system RL1, relay lenses 41 and 44, and the objective lens 46 constitute a Badal optical system. This allows to keep the size of the slit image at the fundus Ef constant, regardless the refractive power of the subject's eye E.

As shown in FIG. 12, a back focal position F1 of the relay lens system RL1 is arranged at a position substantially conjugate optically to the iris of the subject's eye E.

That is, the optical scanner 30, which is arranged at a position substantially conjugate optically to the iris of the subject's eye E as described above, is arranged at the back focal position F1 of the relay lens system RL1 or the vicinity of the back focal position F1. Therefore, even when the slit 22 is moved in the optical axis direction in accordance with the refractive power of the subject's eye E, the size of the slit image (image formed by the light passing through the aperture formed in the slit 22) projected onto the fundus Ef does not change. This means that the projection magnification of the slit image onto the fundus Ef does not change even when the slit 22 moves in the optical axis direction.

As described above, according to the first embodiment, by arranging the optical scanner 30 at the back focal position F1 of the relay lens system RL1 (or the vicinity of the back focal position F1), the Badal optical system is configured with the relay lens system RL1, the relay lenses 41 and 42, and the objective lens 46.

This allows to keep the projected angle of view (projection magnification) of the slit image with reference to the visual axis of the subject's eye E (longitudinal and shorter directions of the slit 22) constant, regardless the refractive power of the subject's eye E. As a result, the size of the slit image does not change regardless of the refractive power of the subject's eye E. This allows to keep the deflection operation speed of the optical scanner 30 constant, and to simplify the control of the optical scanner 30.

In addition, since the projected angle of view (projection magnification) of the slit image with reference to the visual axis of the subject's eye E is constant regardless of the refractive power of the subject's eye, the illumination intensity of the slit image at the fundus Ef can be kept constant regardless of the refractive power of the subject's eye E.

Further, in case of acquiring images at a predetermined imaging angle of view in the ophthalmic apparatus, since the projection magnification is constant as described above, this eliminates the need for a margin of the length in the longitudinal length of the slit 22 provided to acquire a slit image of a predetermined size.

(Relay Lens System RL2)

In addition, as shown in FIG. 6, the relay lens system RL2 is arranged between the slit 22 and the iris aperture 21.

As shown in FIG. 13, the iris aperture 21 is arranged at a front focal position F2 of the relay lens system RL2 or the vicinity of the front focal position F2.

That is, the back focal position F1 of the relay lens system RL1 is the position substantially conjugate optically to the iris aperture 21, and the iris aperture 21 is arranged at the front focal position F2 of the relay lens system RL2. Therefore, the projection magnification from the iris aperture 21 to the optical scanner 30 (arranged at the back focal position F1) is determined by a focal distance f1 of the relay lens system RL1 and a focal distance f2 of the relay lens system RL2. In this case, the projection magnification is (f1/f2).

The ophthalmic apparatus according to the embodiments is required to form images of the iris aperture 21 with a predetermined size on the iris of the subject's eye E. When the projection magnification from the iris of the subject's eye E to the optical scanner 30 via the objective lens 46 is a known projection magnification, an image of the iris aperture 21 of a predetermined size should be projected on the optical scanner 30. In this case, the projection magnification from the iris aperture 21 to the optical scanner 30 is determined by the focal distance f1 of the relay lens system RL1 and the focal distance f2 of the relay lens system RL2. Therefore, by changing at least one of the focal distances f1 and f2, the image of the iris aperture 21 can be easily formed on the iris of the subject's eye E with a predetermined size. In some embodiments, while the focal distance f1 remains fixed, the focal distance f2 is changed alone.

The focal distance f1 is a composite focal distance of the relay lens system RL1. In some embodiments, the relay lens system RL1 includes a plurality of the lenses with different dioptric powers, and changes the focal distance f1 by changing at least one of the lenses constituting the relay lens system RL1. In some embodiments, at least one of the lenses constituting the relay lens system RL1 is a lens whose dioptric power can be changed. Examples of the lens whose dioptric power can be changed include a liquid crystal lens, a liquid lens, and an Alvarez lens. Even when the focal distance f1 is changed, the back focal position of the relay lens system RL1 is arranged at a position substantially conjugate optically to the iris (pupil conjugate position) of the subject's eye E.

The focal distance f2 is a composite focal distance of the relay lens system RL2. In some embodiments, the relay lens system RL2 includes a plurality of the lenses with different dioptric powers, and changes the focal distance f2 by changing at least one of the lenses constituting the relay lens system RL2. In some embodiments, at least one of the lenses constituting the relay lens system RL2 is a lens whose dioptric power can be changed. Even when the focal distance f2 is changed, the front focal position of the relay lens system RL2 is arranged at a position substantially conjugate optically to the iris (pupil conjugate position) of the subject's eye E.

In addition, for imaging the fundus Ef, it is desirable to use a light source that emits a high-intensity light. However, light sources available for general use (light sources that are mass-produced) are limited in the size of the emitting surface (luminous area, output luminous flux cross section size). Thereby, the image of the iris aperture 21 should be projected onto the optical scanner 30 with a projection magnification corresponding to the size of the emitting surface of the light source.

According to this embodiment, by changing at least one of the focal distances f1 and f2, the projecting magnification from the iris aperture 21 and the optical scanner 30 can be changed. Thereby, the image of the iris aperture 21 with any size can be projected onto the optical scanner 30 with the desired size. This allows to project the image of the iris aperture 21 with a desired size onto the optical scanner 30 by simply changing at least one of the focal distances f1 and f2 even when the size of the emitting surface of the light source is different and to improve the degree of freedom in designing optical systems. In particular, this allows to fix the movement amount of the slit 22 in response to changes in the refractive power of the subject's eye E (sensitivity of the movement of the slit 22 in response to changes in the refractive power) by fixing the focal distance f1 and changing the focal distance f2 alone, and to further improve the degree of freedom in designing optical systems.

Further, according to the embodiments, the effective diameter of one or more lenses constituting the relay lens system RL1 can be reduced.

The reason for this is that the slit 22, which is arranged at a position substantially conjugate optically to the fundus Ef of the subject's eye E, is arranged between the optical scanner 30 and the iris aperture 21. The slit 22 can be moved in the optical axis direction in accordance with the refractive power of the subject's eye E. Here, the projection magnification from the iris aperture 21 to the optical scanner 30 is determined by the first distance, which is a distance between the optical scanner 30 and the relay lens system RL1, and the second distance, which is a distance between the iris aperture 21 and the relay lens system RL1. Thereby, when the first distance is shortened, the second distance should also be shortened. However, since it is necessary to maintain the conjugate relationship with the iris and the conjugate relationship with the fundus Ef while securing the space for movement of the slit 22 in the optical axis direction, the first distance becomes longer and the effective diameter of the relay lens system RL1 becomes larger. According to this embodiment, by providing the relay lens system RL2, the projection magnification can be adjusted using the relay lens system RL2 even if the first distance is shortened. This allows to shorten the first distance while maintaining the conjugate relationship with the iris and the conjugate relationship with the fundus Ef and securing the space for movement of the slit 22 in the optical axis direction, and to reduce the effective diameter of the one or more lenses constituting the relay lens system RL1.

Further, since the effective diameter of the one or more lenses constituting the relay lens system RL1 can be reduced, the length of the optical system from the optical scanner 30 to the light source 510 can be reduced.

[Configuration of Control System of Ophthalmic Apparatus 1]

Figure 14:
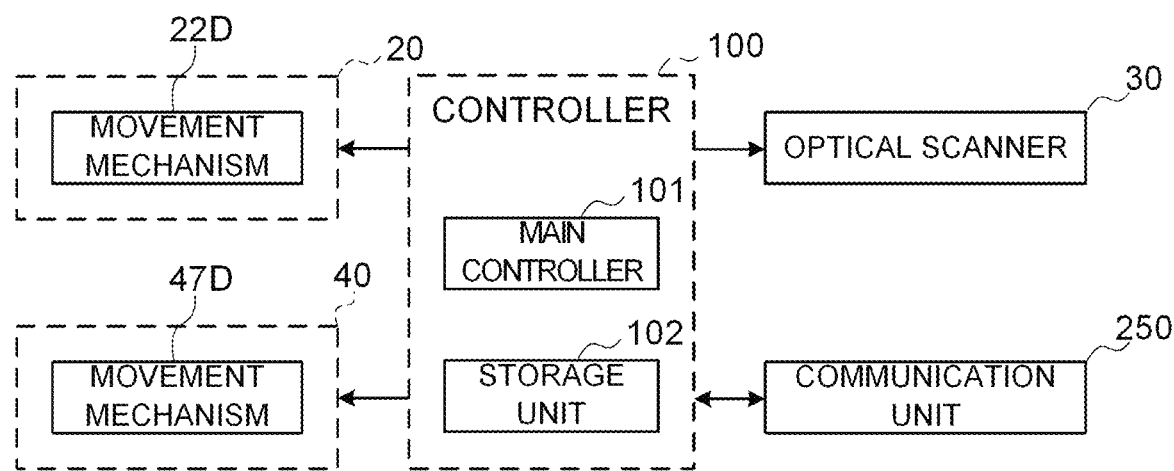
FIG. 14 is a diagram illustrating an example of a configuration of a control system of the ophthalmic apparatus according to the first embodiment.

FIG. 14 shows a block diagram of an example of the configuration of the control system of the ophthalmic apparatus 1 according to the first embodiment. In FIG. 14, like reference numerals designate like parts as in FIG. 2 or FIG. 6. The same description may not be repeated.

As shown in FIG. 14, the control system of the ophthalmic apparatus 1 is configured with a controller 100 as a center.

It should be noted at least part of the configuration of the control system may be included in the optical system in the ophthalmic apparatus 1.

(Controller 100)

The controller 100 controls each part of the ophthalmic apparatus 1. The controller 100 includes a main controller 101 and a storage unit 102. The main controller 101 includes a processor and executes the control processing of each part of the ophthalmic apparatus 1 by executing processing according to the program(s) stored in the storage unit 102.

(Main Controller 101)

The main controller 101 performs control for the illumination optical system 20, control for the optical scanner 30, control for the imaging optical system 40, and control for the communication unit 250.

The control for the illumination optical system 20 includes control for the movement mechanism 22D. The movement mechanism 22D moves the slit 22 in the optical axis direction of the illumination optical system 20. The main controller 101 controls the movement mechanism 22D in accordance with the state of the subject's eye E to arrange the slit 22 at the position corresponding to the state of the subject's eye E. Examples of the state of the subject's eye E includes a shape of the fundus Ef, a refractive power, and an axial length. The refractive power can be obtained from a known eye refractive power measurement apparatus as disclosed in Japanese Unexamined Patent Application No. 61-293430 or Japanese Unexamined Patent Application Publication No. 2010-259495, for example. The axial length can be obtained from a known axial length measurement apparatus or a measurement value acquired by an optical coherence tomography.

For example, the storage unit 102 stores first control information. In the first control information, the positions of the slit 22 on the optical axis of the illumination optical system 20 are associated with the refractive powers in advance. The main controller 101 specifies the position of the slit 22 corresponding to the refractive power by referring to the first control information, and controls the movement mechanism 22D so as to arrange the slit 22 at the specified position.

Here, as the slit 22 moves, the light amount distribution of the light passing through the aperture formed in the slit 22 changes. In this case, the main controller 101 can change at least one of the position of the light source 510 and the orientation of the light source 510 by controlling the controller 550 in the smartphone 500 via the communication unit 250.

For example, as shown in FIG. 11, the position of the slit 22 is moved from the position of the slit 22' before the movement according to the state of the subject's eye E. Thereby, the light amount distribution of the light passing through the aperture formed in the slit 22 changes.

In this case, the main controller 101 controls the communication unit 250 to send communication signal(s) to the smartphone 500, and causes the controller 550 to change at least one of the position of the light source 510 and the orientation of the light source 510. Thereby, the relative position between the light source 510 (incoming opening, smartphone 500) and the iris aperture 21 changes. By changing the relative position between the apertures 21A and 21B, which are formed in the iris aperture 21, and the light source 510, the light amount distribution of the light passing through the apertures 21A and 21B is changed. Further, the light amount distribution of the light, which passes through the apertures 21A and 21B formed in the iris aperture 21, at the aperture formed in the slit 22 is changed.

In some embodiments, the main controller 101 can control the smartphone 500 so as to move the light source 510 based on the refractive power of the subject's eye E as the state of the subject's eye E and the position of the slit 22 after the movement (or movement direction and movement amount of the slit 22 with reference to a reference position).

For example, the storage unit 102 stores second control information. In the second control information, at least one of the positions and the orientations of the light source 510 are associated with the refractive powers and the positions of the slit 22 after the movement (or the movement directions and movement amounts of the slit 22 with reference to the reference position) in advance. The main controller 101 specifies at least one of the position and the orientation of the light source 510 corresponding to the refractive power or the position of the slit 22 after the movement by referring to the second control information, and controls the smartphone 500 so that the light source 510 is arranged at the specified position or in the specified orientation. The main controller 101 controls the communication unit 250 to send communication signal(s) to the smartphone 500 and to change the position and the orientation of the light source 510 in the smartphone 500.

In some embodiments, at least one of the position of the optical element 24 and the orientation of the optical element 24 with respect to the aperture(s) formed in the iris aperture 21 can be changed. For example, the main controller 101 can change the at least one of the position of the optical element 24 and the orientation of the optical element 24 by controlling the movement mechanism that moves the optical element 24.

In FIG. 14, the control for the optical scanner 30 includes control of the scan range (scan start position and scan end position) and the scan speed.

The control for the imaging optical system 40 includes control for a movement mechanism 47D. The movement mechanism 47D moves the focusing lens 47 in the optical axis direction of the imaging optical system 40. The main controller 101 can control the movement mechanism 47D based on an analysis result of the image acquired using the image sensor 520.

Further, the main controller 101 can control the movement mechanism 47D based on a content of operation of the user using an operation unit (not shown).

(Storage Unit 102)

The storage unit 102 stores various computer programs and data. The computer programs include an arithmetic program and a control program for controlling the ophthalmic apparatus 1.

In some embodiments, the ophthalmic apparatus 1 includes at least one of the operation unit and a display unit.

The operation unit includes an operation device and an input device. The operation unit includes buttons and switches (e.g., operation handle, operation knob, etc.) and operation devices (e.g., mouse, keyboard, etc.) provided in the ophthalmic apparatus 1. In addition, the operation unit may include any operation device or any input device, such as a trackball, a control panel, a switch, a button, a dial, etc.

The display unit displays various information on the ophthalmic apparatus 1 (such as setting information of the optical elements). The display unit is configured to include a display device such as a flat panel display such as an LCD (Liquid Crystal Display). In addition, the display unit may include various types of display devices such as a touch panel and the like provided in the housing of the ophthalmic apparatus 1.

It should be noted that the operation unit and the display unit do not need to be configured to be separate devices. For example, a device like a touch panel, which has a display function integrated with an operation function, can be used. In this case, the operation unit includes the touch panel and the computer program. The content of operation performed on the operation unit is fed to the controller 100 as an electric signal. Moreover, operations and inputs of information may be performed using a graphical user interface (GUI) displayed on the display unit and the operation unit. In some embodiments, the functions of the display unit and the operation unit are realized a touch screen.

(Other Configurations)

In some embodiments, the ophthalmic apparatus 1 further includes a fixation projection system. Further, an optical path of the fixation projection system is coupled with the optical path of the imaging optical system 40 in the configuration of the optical system shown in FIG. 1. The fixation projection system can present internal fixation targets or external fixation targets to the subject's eye E. In case of presenting the internal fixation target to the subject's eye E, the fixation projection system includes an LCD that displays the internal fixation target under the control from the controller 100, and projects a fixation light flux output from the LCD onto the fundus Ef of the subject's eye E. The LCD is configured to be capable of changing the display position of the fixation target on the screen of the LCD. By changing the display position of the fixation target on the screen of the LCD, the projected position of the fixation target on the fundus of the subject's eye E can be changed. The display position of the fixation target on the LCD can be designated using the operation unit (not shown) by the user.

In some embodiments, the ophthalmic apparatus 1 includes an alignment system. In some embodiments, the alignment system includes an XY alignment system and a Z alignment system. The XY alignment system is used for position matching between the optical system of the apparatus and the subject's eye E in a direction intersecting the optical axis of the optical system of the apparatus (objective lens 46). The Z alignment system is used for position matching between the optical system of the apparatus and the subject's eye E in a direction of the optical axis of the ophthalmic apparatus 1 (objective lens 46).

For example, the XY alignment system projects a bright spot (bright spot in the infrared region or near-infrared region) onto subject's eye E. The controller 100 acquires an anterior segment image of the subject's eye E on which the bright spot is projected, and obtains the displacement between the bright spot image drawn on the acquired anterior segment image and an alignment reference position. The controller 100 relatively moves the optical system of the apparatus and the subject's eye E in the direction intersecting the direction of the optical axis so as to cancel the obtained displacement, using the movement mechanism.

For example, the Z alignment system projects alignment light in infrared region or the near-infrared region from a position away from the optical axis of the optical system of the apparatus, and receives the alignment light reflected on the anterior segment of the subject's eye E. The controller 100 specifies a distance to the subject's eye E from the optical system of the apparatus from the light receiving position of the alignment light that changes in accordance with the distance to the subject's eye E from the optical system of the apparatus. The controller 100 relatively moves the optical system of the apparatus and the subject's eye E in the direction of the optical axis using the movement mechanism (not shown) so that the specified distance becomes a predetermined working distance.

In some embodiments, the function of the alignment system is realized by two or more anterior segment cameras arranged at positions away from the optical axis of the optical system of the apparatus. For example, as disclosed in Japanese Unexamined Patent Application Publication No. 2013-248376, the controller 100 analyzes the anterior segment images of subject's eye E substantially simultaneously acquired using the two or more anterior segment cameras, and specifies a three-dimensional position of the subject's eye E using known trigonometry. The controller 100 controls the movement mechanism (not shown) to relatively move the optical system of the apparatus and the subject's eye E three-dimensionally so that the optical axis of the optical system of the apparatus substantially coincides with an axis of the subject's eye E and the distance of the optical system of the apparatus with respect to the subject's eye E is a predetermined working distance.

Subsequently, an example of the configuration of the smartphone 500 will be described.

[Configuration of the Smartphone 500]

As shown in FIG. 6, the smartphone 500 includes the light source 510, the image sensor 520, the imaging lens 521, as in FIG. 1.

(Light Source 510)

The light source 510 includes a visible light source that generates light in the visible region. For example, the light source 510 includes a white light source. This type of light source 510 includes, for example, LED (Light Emitting Diode), LD (Laser Diode), halogen lamp, or xenon lamp. In some embodiments, the light source 510 includes a light source capable of outputting light with each color component of RGB. In some embodiments, the light source 510 includes a light source capable of switch to output the light in infrared region or the light in non-infrared region. The light source 510 is arranged at a position non-conjugate optically to each of the fundus Ef and the iris.

(Image Sensor 520)

The image sensor 520 realizes the function as a pixelated photodetector. The light receiving surface (detecting surface, imaging surface) of the image sensor 520 can be arranged at a position substantially conjugate optically to the fundus Ef as an imaging site. As described above, the imaging lens 521 is configured to image the returning light of the illumination light entering the smartphone 500 on the light receiving surface of the image sensor 520.

The result of light reception acquired by the image sensor 520 is read out using a rolling shutter method under the control from the controller 100. This type of image sensor 520 includes a CMOS image sensor as described below, for example.

[Configuration of the Control System of the Smartphone 500]

The control system of the smartphone 500 is configured with a controller 550 as a center, as shown in FIG. 3.

The controller 550 controls each part of the smartphone 500, such as the light source 510, the image sensor 520, the image forming unit 560, and the communication unit 580, as described above.

The control of light reception of the returning light for the image sensor 520 (rolling shutter control) includes reset control, exposure control, charge transfer control, and output control as described below. Further, time Tr required for the reset control, time (exposure time) Te required for the exposure control, time Tc required for the charge transfer control, and time Tout required for the output control, etc., can be changed.

In the following, the rolling shutter control according to the embodiments will be described.

The image sensor 520 includes the CMOS image sensor, as described above. In this case, the image sensor 520 includes a plurality of pixels (light receiving elements) arranged in a plurality of pixel groups in a column direction, the pixel groups being arranged in a row direction. Specifically, the image sensor 520 includes a plurality of pixels arranged two-dimensionally, a plurality of vertical signal lines, and a horizontal signal line. Each pixel includes a photodiode (light receiving element), and a capacitor. The vertical signal line is provided for each pixel group in the column direction (vertical direction) orthogonal to the row direction (horizontal direction). Each of the vertical signal lines is selectively electrically connected to the pixel group in which the electrical charge corresponding to the result of light reception is accumulated. The horizontal signal line is selectively electrically connected to the vertical signal lines. Each of the pixels accumulates the electrical charge corresponding to the result of light reception of the returning light. The accumulated electrical charge is read out sequentially for each pixel group in the row direction, for example. For example, for each line in the row direction, a voltage corresponding to the electrical charge accumulated in each pixel is supplied to the vertical signal line. The vertical signal lines are selectively electrically connected to the horizontal signal line. By performing readout operation for each line in the row direction described above sequentially in the vertical direction, the results of light reception of the plurality of pixels arranged two-dimensionally can be read out.

By capturing (reading out) the results of light reception of the return light using the rolling shutter method for this type of image sensor 520, the light receiving image corresponding to the desired virtual aperture shape extending in the row direction is acquired. Such control is disclosed in, for example, U.S. Pat. No. 8,237,835.

Figure 15:
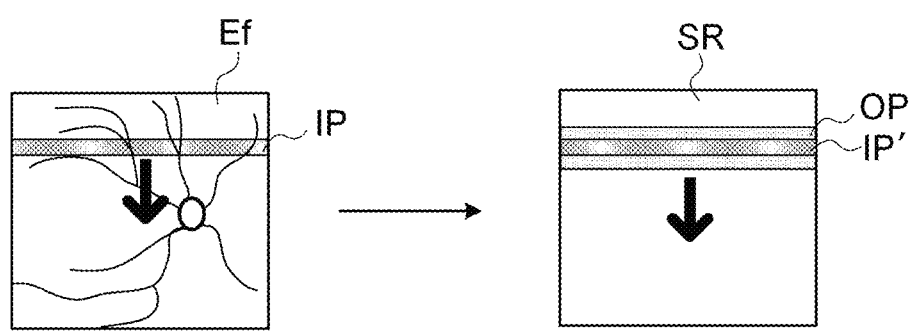
FIG. 15 is an explanatory diagram of an operation of the ophthalmic apparatus according to the first embodiment.

FIG. 15 shows a diagram explaining the operation of the ophthalmic apparatus 1 according to the embodiments. FIG. 15 schematically represents an irradiated range IP of the slit-shaped illumination light irradiated on the fundus Ef and a virtual opening range OP on the light receiving surface SR of the image sensor 520.

For example, the controller 100 in the ophthalmic apparatus 1 deflects the slit-shaped illumination light formed by the illumination optical system 20, using the optical scanner 30. Thereby, the irradiated range IP of the slit-shaped illumination light is sequentially moved in a direction (for example, the vertical direction) orthogonal to the slit direction (for example, the row direction, the horizontal direction) on the fundus Ef.

On the light receiving surface SR of the image sensor 520, by changing the pixels to be read out by the controller 550 of the smartphone 500 in units of lines, the virtual opening range OP is set. The opening range OP is preferable to be the light receiving range IP' of the returning light of the illumination light on the light receiving surface SR or wider than the light receiving range IP'. The controller 550 performs the movement control of the opening range OP in synchronization with the movement control of the irradiated range IP of the illumination light performed by the controller 100. Thereby, without being affected by unnecessary scattered light, high quality images of the fundus Ef with strong contrast can be acquired using a simple configuration.

Figure 16:
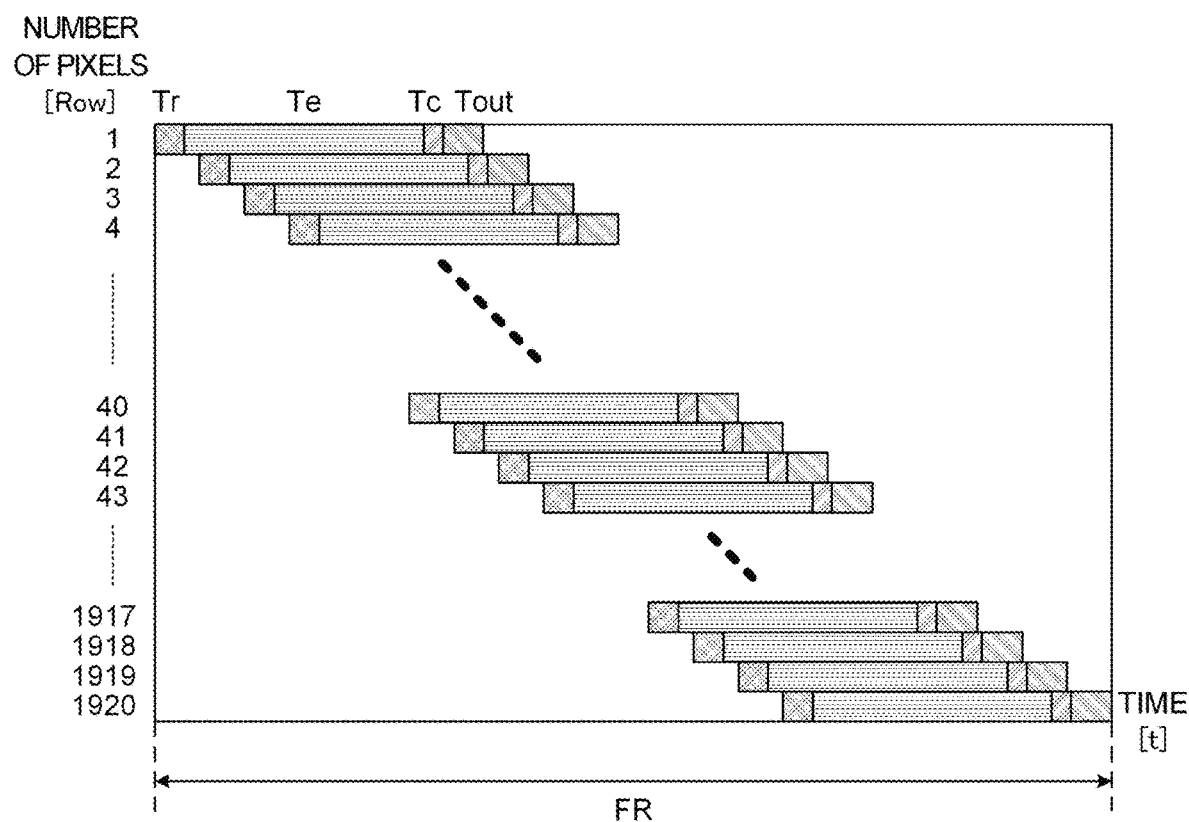
FIG. 16 is an explanatory diagram of an operation of the ophthalmic apparatus according to the first embodiment.
Figure 17:
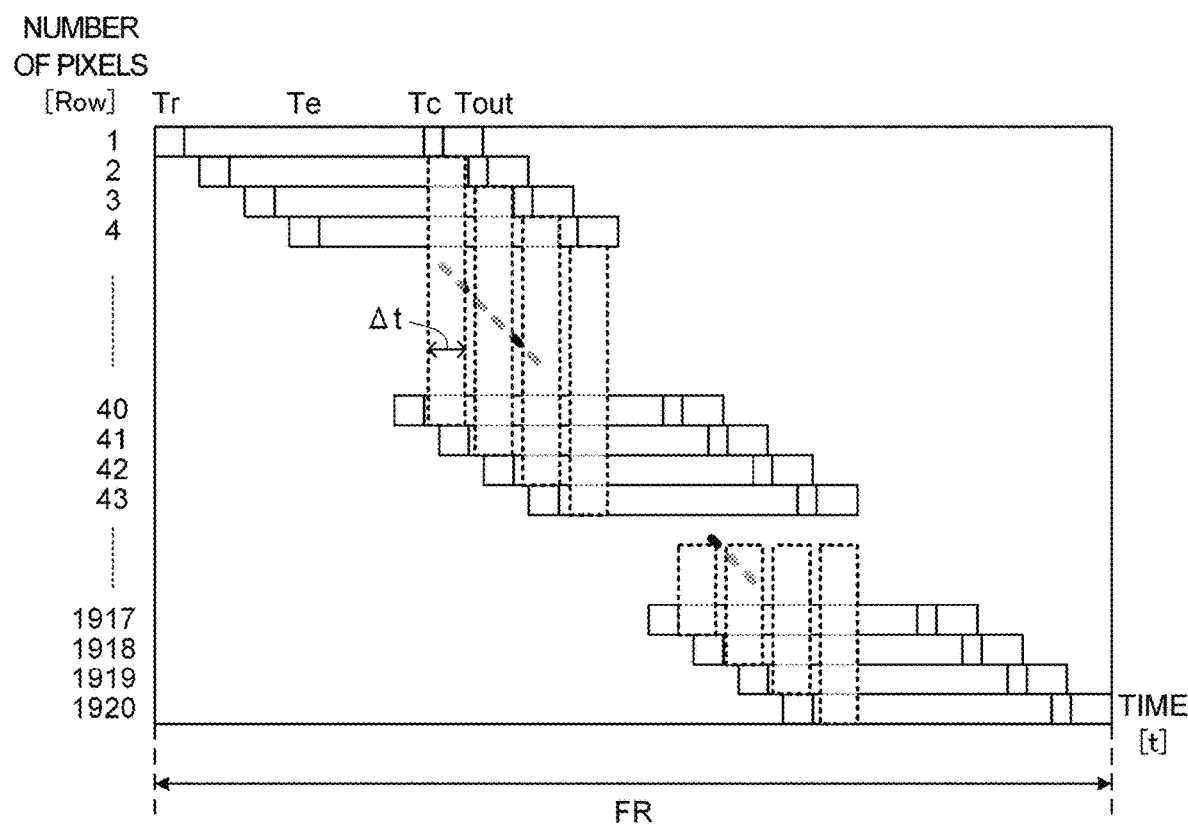
FIG. 17 is an explanatory diagram of an operation of the ophthalmic apparatus according to the first embodiment.

FIGS. 16 and 17 schematically show examples of the control timing of the rolling shutter method for the image sensor 520. FIG. 16 represents an example of the timing of the readout control for the image sensor 520. FIG. 17 represents the timing of the movement control for the irradiated range IP (the light receiving range IP) superimposed on the timing of the readout control in FIG. 16. In FIGS. 16 and 17, the horizontal axis represents the number of rows in the image sensor 520, and the vertical axis represents time.

In addition, in FIGS. 16 and 17, for convenience of explanation, it is assumed that the number of rows in the image sensor 520 is 1920. However, the configuration according to the embodiments is not limited to the number of rows. Further, in FIG. 17, for convenience of explanation, it is assumed that the slit width (width in the row direction) of the slit-shaped illumination light is 40 rows.

The readout control in the row direction includes the reset control, the exposure control, the charge transfer control, and the output control. The reset control is a control that initializes the amount of electrical charge accumulated in the pixels in the row direction. The exposure control is a control that illuminates light on the photodiode and accumulates the electrical charge corresponding to the amount of received light in the capacitor. The charge transfer control is a control that transfers the amount of the electrical charge accumulated in the pixel to the vertical signal line. The output control is a control that outputs the amount of the electrical charge accumulated in the plurality of vertical signal lines via the horizontal signal line. That is, as shown in FIG. 16, the readout time T for reading out the electrical charge accumulated in the pixels in the row direction is the sum of the time Tr required for the reset control, the time Te required for the exposure control (exposure time), the time Tc required for the charge transfer control, and the time Tour required for the output control.

In FIG. 16, by shifting the readout start timing (start timing of time Tc) in units of rows, the light reception results (amount of electrical charge) accumulated in the pixels in the desired range in the image sensor 520 are acquired. For example, in case that the pixel range shown in FIG. 16 is for a single frame of the image, the frame rate FR is determined uniquely.

In this embodiment, the irradiated position of the illumination light on the fundus Ef, the illumination light having a slit width of a plurality of rows, is sequentially shifted in a direction corresponding to the column direction on the fundus Ef.

for example, as shown in FIG. 17, at each predetermined shift time Δt, the irradiated position of the illumination light on the fundus Ef is shifted in row units in the direction corresponding to the column direction. The shift time Δt is obtained by dividing the exposure time Te of the pixel in the image sensor 520 by the slit width of the illumination light (e.g., 40) (Δt=Te/40). Synchronized with this movement timing of this irradiated position, the readout start timing of each row of pixels is delayed and is started for each row in units of shift time Δt. This allows to acquired high quality images of the fundus Ef with strong contrast in a short time with a simple control.

In some embodiments, the image sensor 520 is configured using one or more line sensors.

The control performed by the controller 550 in the smartphone 500 for the image forming unit 560 includes a control that forms a light receiving image corresponding to an arbitrary opening range based on the light reception result(s) read out from the image sensor 520 using the rolling shutter method.

The image forming unit 560 forms the light receiving image corresponding to the arbitrary opening range based on the light reception result(s) read out from the image sensor 520 using the rolling shutter method under the control from the controller 550. The image forming unit 560 can sequentially form light receiving light images corresponding to the opening ranges and form an image of the subject's eye E from a plurality of formed light receiving images.

The image forming unit 560 includes one or more processors and executes the function described above by performing processing corresponding to the program(s) stored in the storage unit or the like.

The relay lens system RL1 is an example of the "first relay lens system" according to the embodiments. The relay lens system RL2 is an example of the "second relay lens system" according to the embodiments. The image sensor 520 is an example of the "sensor" according to the embodiments.

[Operation]

Next, the operation of the ophthalmic apparatus 1 will be described.

Figure 18:
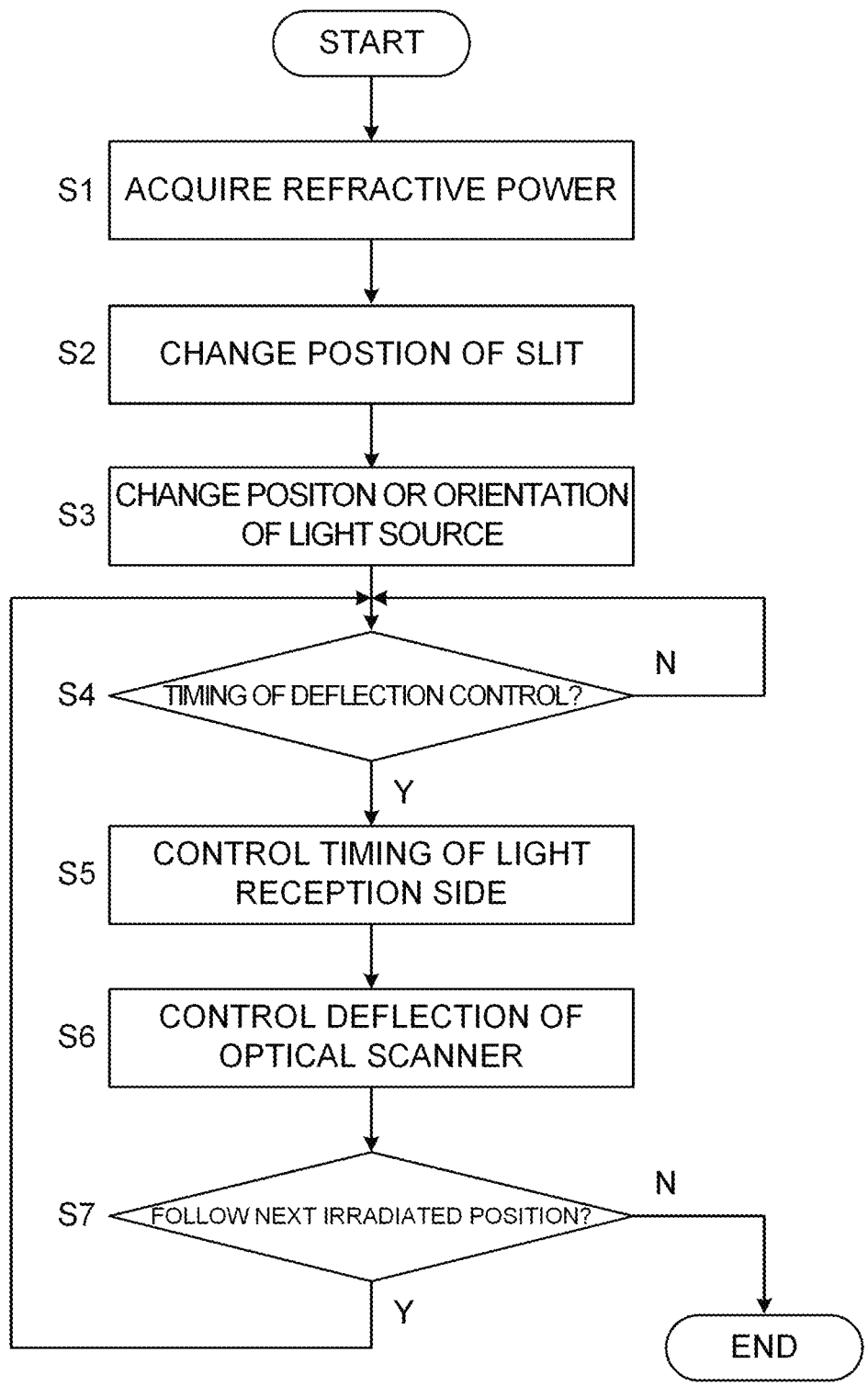
FIG. 18 is a flowchart illustrating an example of an operation of the ophthalmic apparatus according to the first embodiment.

FIG. 18 shows a flowchart of an example of the operation of the ophthalmic apparatus 1 according to the first embodiment. The storage unit 102 stores a computer program for realizing the processing shown in FIG. 18. The main controller 101 operates according to the computer programs, and thereby the main controller 101 performs the processing shown in FIG. 18.

Here, it is assumed that the alignment of the optical system of the apparatus with respect the subject's eye E using the alignment system (not shown) is completed, and that the fixation target is projected onto the fundus of the subject's eye E to guide the subject's eye E to a desired fixation position using the fixation projection system (not shown).

(S1: Acquire Refractive Power)

First, the main controller 101 acquires the refractive power of the subject's eye E from an external ophthalmic measurement apparatus or an electronic medical record.

(S2: Change Position of Slit)

Next, the main controller 101 changes the position of the slit 22 on the optical axis of the illumination optical system 20 in accordance with the refractive power of the subject's eye E acquired in step S1.

Specifically, the main controller 101 specifies the position of the slit 22 corresponding to the refractive power by referring to the first control information stored in the storage unit 102, and controls the movement mechanism 22D so as to arrange the slit 22 at the specified position.

(S3: Change Position or Orientation of Light Source)

Subsequently, the main controller 101 changes at least one of the position of the light source 510 in the smartphone 500 and the orientation of the light source 510 in accordance with the new position of the slit 22 whose position on the optical axis has been changed in step S2.

Specifically, the main controller 101 specifies at least one of the position and the orientation of the light source 510 that correspond to the refractive power or the position of the slit 22 after the movement, by referring to the second control information stored in the storage unit 102. Then, the main controller 101 controls the communication unit 250 to send communication signal(s) to the smartphone 500. The controller 550 in the smartphone 500 controls the movement mechanism so as to arrange the light source 510 at the specified position or in the specified orientation.

(S4: Timing of Deflection Control?)

After step S3, when imaging of the fundus Ef of the subject's eye E is started, the main controller 101 determines whether or not it is a predetermined timing of the deflection control. For example, the main controller 101 presets deflection control information for the optical scanner 30. The deflection control information includes the deflection angle range of the illumination light and deflection speed (deflection frequency) of the illumination light. The main controller 101 specifies the timing of the deflection control based on the preset deflection control information, with reference to the imaging start timing.

When it is determined that it is not the timing of the deflection control (S4: N), the operation of the ophthalmic apparatus 1 repeats step S4. When it is determined that it is the timing of the deflection control (S4: Y), the operation of the ophthalmic apparatus 1 proceeds to step S5.

(S5: Control Timing of Light Reception Side)

When it is determined that it is the timing of the deflection control in step S4 (S4: Y), the main controller 101 controls the communication unit 250 to transmit communication signal(s) for controlling the timing of light reception using the image sensor 520 to the smartphone 500.

The controller 550 in the smartphone 500 receives the communication signal(s) from the ophthalmic apparatus 1, and performs control of light reception described above at the timing corresponding to the received communication signal(s).

(S6: Control Deflection of Optical Scanner)

Subsequently, the main controller 101 controls the optical scanner 30 so that the deflection angle of the deflection surface of the optical scanner 30 is deflected by a predetermined angle step to synchronize with the control timing of the light reception side transmitted in step S5.

Thereby, the illumination light is irradiated at the irradiated position on the fundus Ef corresponding to the deflection angle of the deflection surface of the optical scanner 30. At a designated timing in step S5, the controller 550 in the smartphone 500 causes the light reception result(s) of the pixels in the opening range of the image sensor 520 corresponding to the illuminated range of the illumination light on the fundus Ef performed in step S6 to be acquired.

(S7: Follow Next Irradiated Position?)

The main controller 101 determines whether or not the next irradiated position is to be irradiated with the illumination light. The main controller 101 can determine whether or not the next irradiate position is to be irradiated with the illumination light, by determining whether or not the irradiated range of the illumination light that is moved sequentially has covered a predetermined imaging range of the fundus Ef.

When it is determined that the next irradiate position is to be irradiated with the illumination light (S7: Y), the operation of the ophthalmic apparatus 1 proceeds to step S4. When it is determined that the next irradiate position is not to be irradiated with the illumination light (S7: N), the operation of the ophthalmic apparatus 1 is terminated (END).

By repeating steps S4 to S7, the slit-shaped illumination light is sequentially irradiated on a desired irradiated range on the fundus Ef, and the light reception results are read out from the image sensor 520 corresponding to the irradiated range of the illumination light.

In some embodiments, in step S6, the illumination light is irradiated on the irradiated range set so as to have an overlapping region with the adjacent irradiated range.

Thereby, the fundus image for one frame is formed by composing the overlapping regions so as to overlap with each other.

As described above, according to the first embodiment, the ophthalmic apparatus 1 reads out the light reception results of the imaging elements corresponding to the irradiated positions of the illumination light from the image sensor 520 in the smartphone 500, which is an external device, in synchronization with the timings of the deflection control for the optical scanner 30. This allows to simplify the configuration of the ophthalmic apparatus, and to acquire high quality images of the subject's eye E using rolling shutter method.

Second Embodiment

The configuration of the ophthalmic apparatus according to the embodiments and the configuration of the ophthalmic system according to the embodiments are not limited to the configuration described in the first embodiment. For example, the ophthalmic apparatus according to the embodiments may include a light source and may generate the illumination light using light from the light source.

In the following, the second embodiment will be described with a focus on differences from the first embodiment.

Figure 19:
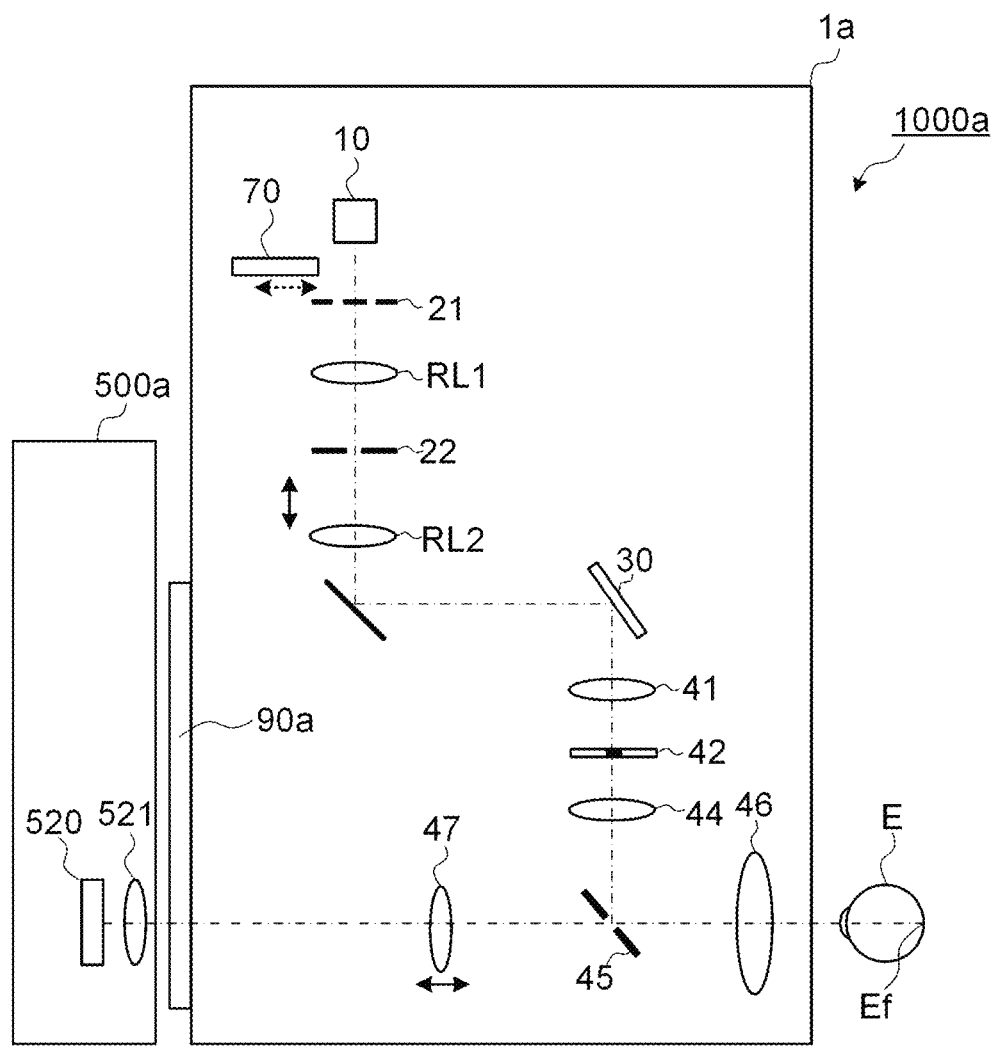
FIG. 19 is a schematic diagram illustrating an example of a configuration of the ophthalmic system according to a second embodiment._

FIG. 19 shows an example of a configuration of the ophthalmic system according to a second embodiment. In FIG. 19, like reference numerals designate like parts as in FIG. 1. The same description may not be repeated.

An ophthalmic system 1000a according to the second embodiment includes a smartphone 500a and an ophthalmic apparatus 1a.

The configuration of the smartphone 500a differs from the configuration of the smartphone 500 shown in FIG. 1 in that the configuration of the smartphone 500a does not include the light source 510. However, the smartphone 500a may include a light source that is not the target to be performed of rolling shutter control according to the embodiments. The configuration of the ophthalmic apparatus 1a differs from the configuration of the ophthalmic apparatus 1 shown in FIG. 1 in that the configuration of the ophthalmic apparatus 1a includes the light source 10. The light source 10 realizes the functions of the light source 510.

It should be noted that, in the same way as the first embodiment, on the surface of the ophthalmic apparatus 1a, a mounting unit 90a for mounting the smartphone 500a is provided. The mounting unit 90a is configured to be capable of holding the smartphone 500a by a known method. The mounting unit 90a differs from the mounting unit 90 in that the mounting unit 90a (and the housing of the ophthalmic apparatus 1a) has an incoming/outgoing opening and an outgoing opening.

In the ophthalmic apparatus 1a, the light from the light source 10 is irradiated on the slit 22. On an optical path between the slit 22 and the light source 10, a wavelength selective filter 70 is provided so as to be capable of inserting and removing from the optical path.

The operation of the ophthalmic system 1000a according to the second embodiment differs from the operation of the ophthalmic system 1000 in that the controller in the ophthalmic apparatus 1a performs the same control for the light source 10 as the controller 550 in the smartphone 500 performs for the light source 510 in the first embodiment.

According to the second embodiment, similar to the first embodiment, this allows to simplify the configuration of the ophthalmic apparatus, and to acquire high quality images of the subject's eye E using rolling shutter method.

Third Embodiment

In the embodiments described above, the case where the optical path of the illumination light and the optical path of the returning light of the illumination light are combined using the perforated mirror has been described. However, the configuration according to the embodiments is not limited thereto. For example, the optical path of the illumination light and the optical path of the returning light of the illumination light may be combined using a beam splitter.

In the following, the third embodiment will be described with a focus on differences from the first embodiment.

Figure 20:
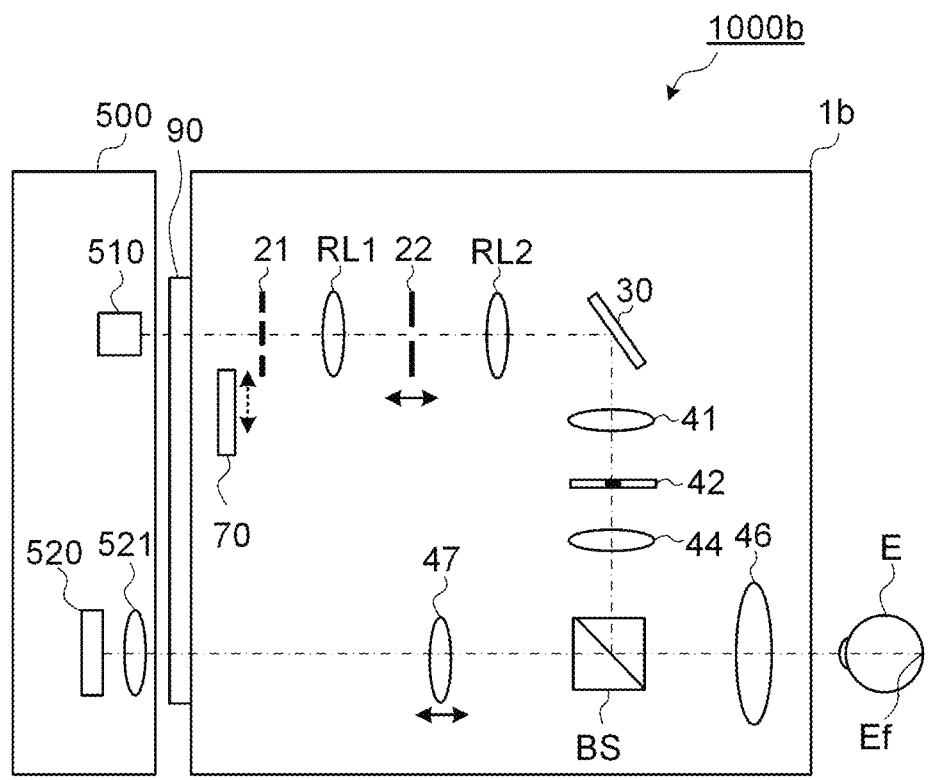
FIG. 20 is a schematic diagram illustrating an example of a configuration of an ophthalmic system according to a third embodiment.

FIG. 20 shows an example of a configuration of the ophthalmic system according to a third embodiment. In FIG. 20, like reference numerals designate like parts as in FIG. 1. The same description may not be repeated.

An ophthalmic system 1000b according to the third embodiment includes a smartphone 500 and an ophthalmic apparatus 1b.

The configuration of the ophthalmic apparatus 1b differs from the configuration of the ophthalmic apparatus 1 shown in FIG. 1 in that a beam splitter BS is provided in place of the perforated mirror 45 in the ophthalmic apparatus 1b. The beam splitter BS reflects the illumination light generated using the light from the light source 510 toward the objective lens 46, and transmits the returning light of the illumination light from the objective lens 46 to the focusing lens 47.

The operation of the ophthalmic system 1000b according to the third embodiment is the same as the operation of the ophthalmic system 1000. Therefore, the detailed description is not repeated here.

According to the third embodiment, similar to the first embodiment, this allows to simplify the configuration of the ophthalmic apparatus, and to acquire high quality images of the subject's eye E using rolling shutter method.

Fourth Embodiment

In the above embodiments, the case where the fundus Ef is scanned by moving the irradiated position of the slit-shaped illumination on the fundus Ef using the optical scanner 30. However, the configuration according to the embodiments is not limited thereto. For example, the fundus Ef may be scanned by modulating the light from the light source using an optical modulator.

In the following, the fourth embodiment will be described with a focus on differences from the first embodiment.

Figure 21:
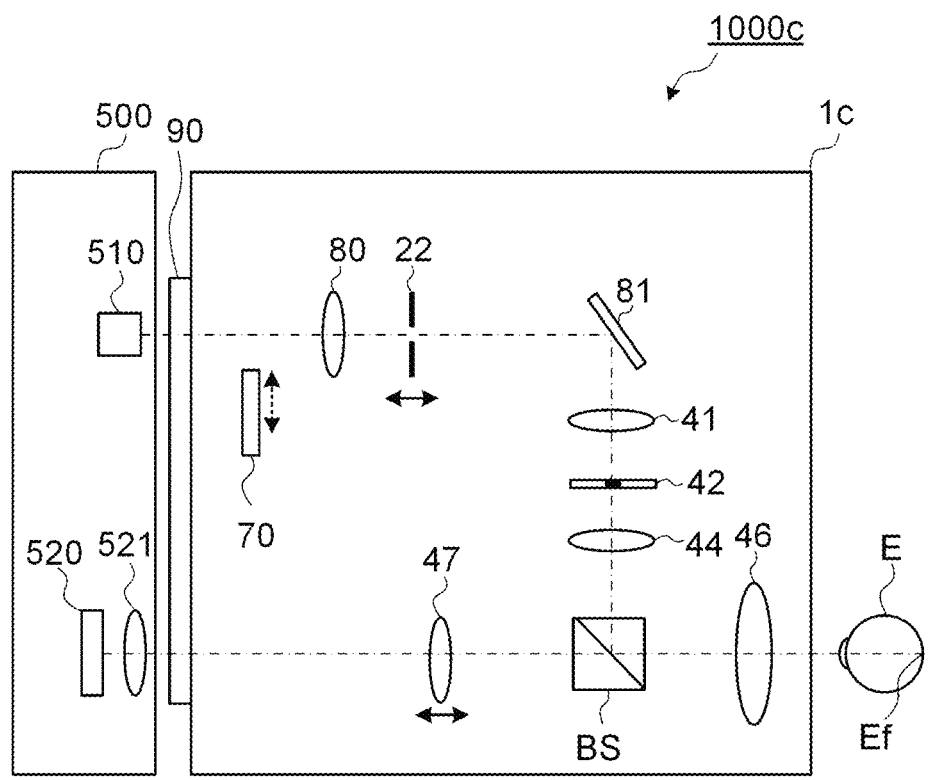
FIG. 21 is a schematic diagram illustrating an example of a configuration of an ophthalmic system according to a fourth embodiment.

FIG. 21 shows an example of a configuration of the ophthalmic system according to a fourth embodiment. In FIG. 21, like reference numerals designate like parts as in FIG. 1. The same description may not be repeated.

An ophthalmic system 1000c according to the fourth embodiment includes a smartphone 500 and an ophthalmic apparatus 1c.

The configuration of the ophthalmic apparatus 1c differs from the configuration of the ophthalmic apparatus 1 shown in FIG. 1 in that a condenser lens 80 is provided in place of the iris aperture 21 in the ophthalmic apparatus 1c and that an optical modulator 81 is provides in place of the optical scanner 30 in the ophthalmic apparatus 1c. The optical modulator 81 can be arranged at a position substantially conjugate optically to an imaging site (for example, fundus Ef) of the subject's eye E. In some embodiments, the ophthalmic apparatus 1c is provided with at least one of the relay lens systems RL1 and RL2, in the same way as in FIG. 1.

The condenser lens 80 converges the light from the light source 510 passing through the incoming opening formed in the mounting unit 90 of the ophthalmic apparatus 1b. The light converged by the condenser lens 80 passes through the aperture formed in the slit 22 and is guided to the optical modulator 81 as the slit-shaped illumination light.

The optical modulator 81 modulates the slit-shaped illumination light formed using the slit 22, under the control from the controller. Examples of the optical modulator 81 include a device using micro electro mechanical systems (MEMS), a digital mirror device (DMD), a spatial light modulator (SLM). The spatial light modulator changes the spatial distribution of the light from the light source.

The operation of the ophthalmic system 1000c according to the fourth embodiment differs from the operation of the ophthalmic system 1000 in that the control is performed on the optical modulator 81 instead of the optical scanner 30 to scan the irradiated position of the illuminating light on the fundus Ef as in the first embodiment.

According to the fourth embodiment, similar to the first embodiment, this allows to simplify the configuration of the ophthalmic apparatus, and to acquire high quality images of the subject's eye E using rolling shutter method.

In addition, in the first to the fourth embodiments, the case where the focus is adjusted by moving the focusing lens 47 along the optical axis mainly has been described. However, the objective lens 46, or an optical element (lens, etc.) other than the focusing lens 47 may be moved along the optical axis.

Further, in the first to the forth embodiments, the ophthalmic apparatus may store setting information of the optical element corresponding to the smartphone including the image sensor. In this case, the ophthalmic apparatus can read out the setting information corresponding to the smartphone before performing the imaging, and can change the arrangement of the optical element, etc. based on the read out setting information.

Further, in the first to the forth embodiments, the ophthalmic apparatus may store setting information of the optical element corresponding to the smartphone, which includes the image sensor, and the subject's eye (subject). In this case, the ophthalmic apparatus can read out the setting information corresponding to the smartphone and the subject's eye before performing the imaging, and can change the arrangement of the optical element, etc. based on the read out setting information.

Further, in the first embodiment, the third embodiment, and the fourth embodiment, the smartphone 500 may be configured to be capable of changing the relative position of the light source 510 to the outgoing opening formed in the housing. In this case, the controller 550 changes the relative position of the light source 510 to the outgoing opening, by moving the movement mechanism that relatively moves the light source 510 with reference to the outgoing opening.

Further, in the first to the fourth embodiments, the smartphone may be configured to be capable of changing the relative position of the image sensor 520 to the incoming opening formed in the housing. In this case, the controller in the smartphone changes the relative position of the image sensor 520 to the incoming opening, by moving the movement mechanism that relatively moves the image sensor 520 with reference to the incoming opening.

Fifth Embodiment

For example, the image data of the subject's eye E acquired using the ophthalmic system according to the above embodiments is configured to be managed in a server that can be connected via a network.

Figure 22:
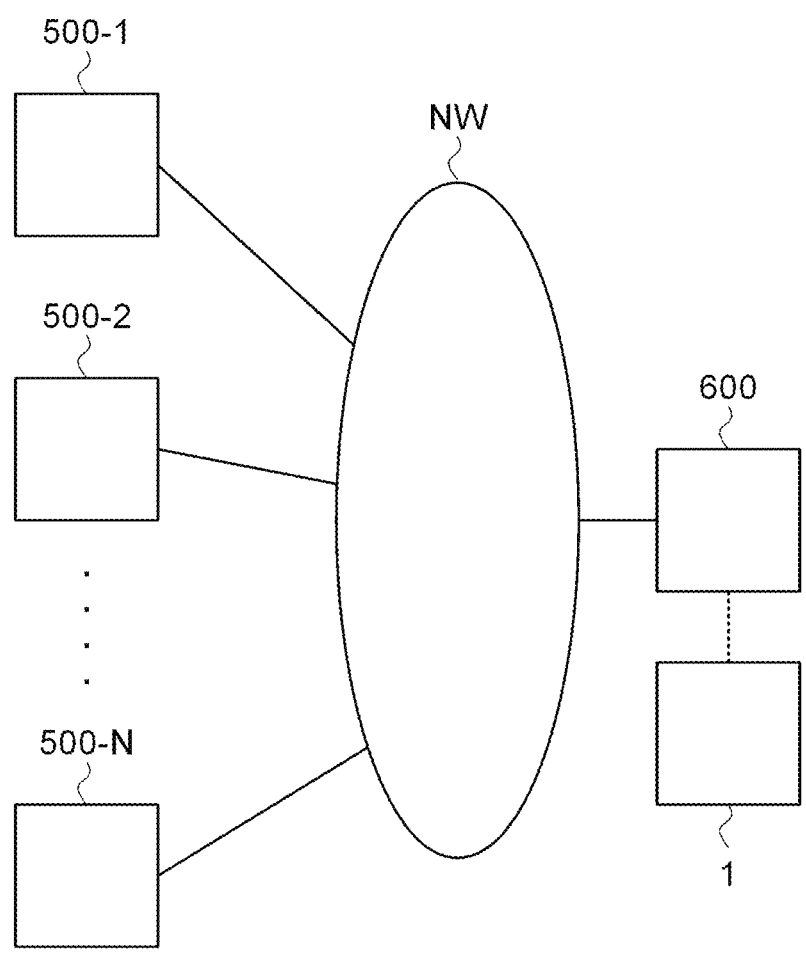
FIG. 22 is a schematic diagram for explaining an the ophthalmic system according to a fifth embodiment.

FIG. 22 shows an example of a configuration of a network system to which the ophthalmic system according to the above embodiments is applied. In FIG. 22, like reference numerals designate like parts as in FIG. 1. The same description may not be repeated.

A network system according to a fifth embodiment includes smartphones 500-1 to 500-N (N is an integer greater than or equal to 1) and a server 600. The smartphones 500-1 to 500-N can communicate and connect to the server 600 via the network NW. The network NW may be the same network as the communication network between the ophthalmic apparatus and the smartphone in the embodiments described above, or a different network.

The smartphones 500-1 to 500-N are the smartphones of any of the first to fourth embodiments. The server 600 includes a controller and a storage unit. The controller can acquire the image data obtained in any of the smartphones 500-1 to 500-N via the network NW, and can store the acquired image data in the storage unit.

Each of the smartphones 500-1 to 500-N acquires the image data of the subject's eye E using the ophthalmic apparatus according to any one of the first to fourth embodiments. Each of the smartphones 500-1 to 500-N encrypts (keeps a secret) the acquired image data, and sends the encrypted image data to the server 600 via the network NW. The server 600 stores the image data sent by each of the smartphones 500-1 to 500-N.

In some embodiments, each smartphone encrypts the image data of the subject's eye E using a predetermined public key. The server 600, or an information processing apparatus that obtained the encrypted image data from the server 600, decrypts the image data of the subject's eye E using a private key corresponding to this public key. Examples of the predetermined public key include a public key that has been created in advance corresponding to the smartphone that the image data of the subject's eye E has been acquired, the ophthalmic apparatus used for acquiring the image data of the subject's eye E, the subject's eye E (subject), the examiner, the imaging process (inspection process) in that the image data of the subject's eye E has been acquired, or a combination of two or more of these. In this case, the private key, that is paired with the created public key, is simultaneously created.

In some embodiments, the encrypted image data of the subject's eye E is stored in the server 600 associated with a predetermined identification information. In this case, the server 600, or an information processing apparatus that obtained the encrypted image data from the server 600, specifies the private key corresponding to the public key used for encrypting the image data based on the identification information associated with the image data of the subject's eye E, and decrypts the image data of the subject's eye E using the specified private key. For example, the identification information described above is configured to be communicated via the communication connection established between the server 600 and the ophthalmic apparatus. For example, in the server 600, the identification information described above is designated using an operation unit (not shown). Examples of the predetermined identification information include first identification information of the smartphone that the image data of the subject's eye E has been acquired, second identification information of the ophthalmic apparatus used for acquiring the image data of the subject's eye E, third identification information for identifying the subject's eye E (subject), fourth identification information for identifying the examiner, fifth identification information for identifying the imaging process (inspection process) in that the image data of the subject's eye E has been acquired, and a sixth identification information including a combination of two or more of the first to the fifth identification information.

In some embodiments, the server 600 is configured to authenticate the information processing apparatus accessing the image data of the subject's eye E using any of the first to sixth identification information described above, and to provide requested image data to the authenticated information processing apparatus. In case of encrypting the provided image data using the public key as described above, the information processing apparatus can decrypt the image data provided from the server 600 using the private key corresponding to the public key.

In some embodiments, the smartphone includes an operation unit and a display unit, and is configured to display the acquired image of the subject's eye E on the display unit using the operation unit. In some embodiments, the smartphone has a function that prohibits the display of the acquired image of the subject's eye E and sends the image to the server 600.

As described above, the image data of the subject's eye E acquired using the smartphone can be managed in the server 600. In particular, the image data acquired in the smartphone can be protected properly.

[Actions]

The ophthalmic apparatus and the ophthalmic system according to the embodiments will be described.

An ophthalmic apparatus (1, 1a, 1b, 1c) according to some embodiments includes an objective lens (46), an illumination optical system (20), a mounting unit (90, 90a), an imaging optical system (40), a communication unit (250), and a controller (100, main controller 101). The illumination optical system is configured to generate illumination light using light from a light source (510, 10), and to illuminate a subject's eye (E) with the illumination light through the objective lens. The mounting unit is configured to allow an external device (smartphone 500, smartphone 500a) including a sensor (image sensor 520) to be mounted so that the sensor is arranged on an imaging optical path (optical path of the imaging optical system 40). The imaging optical system is configured to guide returning light of the illumination light from the subject's eye to the imaging optical path. The communication unit has a communication function with the external device. The controller is configured to control the illumination optical system and to control the sensor through the communication unit to synchronize with control for the illumination optical system.

According to such an aspect, with the external device having the sensor attached, the controller controls the illumination optical system and also controls the sensor through the communication unit to synchronize with the control for the illumination optical system. This allows to simplify the configuration of the ophthalmic apparatus, and to acquire high quality images of the subject's eye.

An ophthalmic apparatus (1, 1a, 1b, 1c) according to some embodiments includes an objective lens (46), an illumination optical system (20), a mounting unit (90, 90a), an imaging optical system (40), a communication unit (250), and a controller (100, main controller 101). The illumination optical system is configured to generate illumination light using light from a light source (510, 10), and to illuminate a subject's eye (E) with the illumination light through the objective lens. The mounting unit is configured to allow an external device (smartphone 500, smartphone 500a) including a sensor (image sensor 520) to be mounted so that the sensor is arranged on an imaging optical path (optical path of the imaging optical system 40). The imaging optical system is configured to guide returning light of the illumination light from the subject's eye to the imaging optical path. The communication unit has a communication function with the external device. The controller is configured to control at least the illumination optical system, under control of the external device through the communication unit.

According to such an aspect, with the external device having the sensor attached, the controller controls the illumination optical system under the control from the external device through the communication unit. This allows to simplify the configuration of the ophthalmic apparatus, and to acquire high quality images of the subject's eye.

In some embodiments, the illumination optical system includes an optical modulator (81) configured to be capable of being arranged at a position substantially conjugate optically to an imaging site (fundus Ef) of the subject's eye, and to generate the illumination light by modulating the light from the light source, and the controller is configured to control the optical modulator in synchronization with control for the sensor.

According to such an aspect, the control for the optical modulator and the control for the sensor in the external device are synchronized. Thereby, the configuration of the ophthalmic apparatus can be simplified and high quality images of the subject's eye can be acquired using the rolling shutter method.

In some embodiments, the illumination optical system includes a slit (22) in that a slit-shaped aperture is formed, the slit-shaped aperture being capable of being arranged at a position substantially conjugate optically to an imaging site of the subject's eye, an iris aperture (21) arranged between the light source and the slit, and configured to be capable of being arranged at a position substantially conjugate optically to an iris of the subject's eye; and an optical scanner (30) deflecting the illumination light that has passed through the aperture, the optical scanner being capable of being arranged at a position substantially conjugate optically to the iris of the subject's eye, and the controller is configured to control the optical scanner in synchronization with control for the sensor.

According to such an aspect, the deflection control for the optical scanner and the control for the sensor in the external device are synchronized. Thereby, the configuration of the ophthalmic apparatus can be simplified and high quality images of the subject's eye can be acquired using the rolling shutter method.

In some embodiments, the illumination optical system includes a first relay lens system (relay lens system RL1) arranged between the optical scanner and the slit, and a back focal position of the first relay lens system is a position substantially conjugate optically to the iris.

According to such an aspect, the optical system from the first relay lens system to the iris of the subject's eye can be configured according to the Badal's principle. Thereby, even when the slit is moved in the optical axis direction in accordance with the refractive power of the subject's eye, the size of the slit image project onto an attention site of the subject's eye does not change, regardless of the refractive power of the subject's eye. This means that the projection magnification of the slit image onto the attention site does not change even when the slit moves in the optical axis direction. As a result, regardless of the refractive power of the subject's eye, this allows to keep the deflection operation speed of the optical scanner constant, and to simplify the control of the optical scanner. In addition, since the projected angle of view (projection magnification) of the slit image with reference to the visual axis of the subject's eye is constant regardless of the refractive power of the subject's eye, the illumination intensity of the slit image at the attention site can be kept constant regardless of the refractive power of the subject's eye. Further, in case of acquiring images at a predetermined imaging angle of view in the ophthalmic apparatus, since the projection magnification is constant, this eliminates the need for a margin longitudinal length of the slit provided to acquire a slit image of a predetermined size.

In some embodiments, the optical scanner is arranged at the back focal position or the vicinity of the back focal position.

According to such an aspect, regardless of the refractive power of the subject's eye, this allows to keep the deflection operation speed of the optical scanner constant while reducing the size of the optical scanner, and to simplify the control of the optical scanner.

In some embodiments, the illumination optical system includes a second relay lens system (relay lens system RL2) arranged between the slit and the iris aperture, and the iris aperture is arranged at a front focal position of the second relay lens system or the vicinity of the front focal position of the second relay lens system.

According to such an aspect, by changing the focal distance of the first relay lens system or the focal distance of the second relay lens system, the projection magnification from the iris aperture to the optical scanner can be changed. Thereby, the image of the iris aperture with any size can be projected onto the optical scanner with a desired size. This allows to project the image of the iris aperture with the desired size onto the optical scanner even when the size of the emitting surface of the light source is different, and to improve the degree of freedom in designing optical systems.

In some embodiments, one or more apertures (21A, 21B) that the illumination light passes through are formed in the iris aperture so that luminous flux cross section of the illumination light and luminous flux cross section of returning light from the subject's eye are separated on a cornea of the subject's eye, an anterior surface of lens of the subject's eye, and a posterior surface of lens of the subject's eye.

According to such an aspect, by pupil-dividing the illumination light incident on the subject's eye and the returning light from the subject's eye with a high degree of accuracy, the illumination required for measuring the attention site of the subject's eye can be secured and high quality image of the subject's eye can be acquired, with a simple configuration, without being affected by the state of the subject's eye.

In some embodiments, two or more apertures are formed in the iris aperture, and the two or more apertures are formed in linear symmetry to a straight line, the straight line passing through an optical axis of the illumination optical system and extending in a direction corresponding to a longitudinal direction of the aperture formed in the slit.

According to such an aspect, the illumination light incident on the subject's eye from different directions and the returning light from the subject's eye can be perform pupil division with a high degree of accuracy.

In some embodiments, the aperture has a circular segment shape, and a direction of a chord of the circular segment shape is approximately parallel to a direction corresponding to the longitudinal direction of the aperture formed in the slit.

According to such an configuration, the light amount of illumination light can be increased and high quality images with stronger contrast can be acquired, with a simple configuration.

The ophthalmic apparatus according to some embodiments further includes the light source (10).

According to such an aspect, by diverting the sensor in the external device, the configuration of the ophthalmic apparatus can be simplified and high quality images of the subject's eye can be acquired.

In some embodiments, the external device includes a light source (510), and the mounting unit is configured to allow the external device to be mounted so that the light source is arranged on an optical path of the illumination optical system.

According to such an aspect, by diverting the light source and the sensor in the external device, the configuration of the ophthalmic apparatus can be simplified and high quality images of the subject's eye can be acquired.

The ophthalmic apparatus according to some embodiments includes a wavelength selective filter (70) configured to be capable of inserting into or removing from an optical path of the illumination optical system.

According to such an aspect, the imaging site can be illuminated with the illumination light having wavelength component(s) within a desired wavelength range, and the ophthalmic apparatus capable of observing the subject's eye in detail can be provided.

In some embodiments, the external device is a mobile phone or a portable information terminal.

According to such an aspect, the control for the illumination optical system and the control for the sensor are synchronized using the mobile phone or the portable information terminal. This allows to simplify the configuration of the ophthalmic apparatus and to acquire high quality images of the subject's eye.

An ophthalmic system (1000, 1000a, 1000b, 1000c) according to some embodiments includes the external device and the ophthalmic apparatus described any one of the above.

According to such an aspect, with the external device with the sensor attached, the control for the illumination optical system and the control for the sensor are synchronized. Thereby, the configuration of the ophthalmic apparatus can be simplified and high quality images of the subject's eye can be acquired.

The above-described some embodiments or the modification examples thereof are merely examples for carrying out the present invention. Those who intend to implement the present invention can apply any modification, omission, addition, or the like within the scope of the gist of the present invention.

In the above embodiments, the case where the rolling shutter control is performed using the image sensor 520 has been mainly described. However, the configuration according to the embodiments is not limited thereto. For example, the configuration according to the embodiments can also be applied to the case where global shutter control is performed using image sensor 520.

In the above embodiments, a detection means for detecting the attachment of the smartphone using the mounting unit may be provided, and when the attachment of the smartphone is detected by the detection means, the communication connection between the ophthalmic apparatus and the smartphone may be established. Further, the detection result obtained by the detection means can also be notified to the ophthalmic apparatus or the smartphone (display, sound output, light emission, etc.). In this case, upon receiving the notification of the detection result, the user can establish the communication connection between the ophthalmic apparatus and the smartphone.

In the above embodiments, the ophthalmic apparatus may have arbitrary functions adaptable in the field of ophthalmology. Examples of such functions include a axial length measurement function, a tonometry function, an optical coherence tomography (OCT) function, an ultrasonic inspection, and the like. It should be noted that the axial length measurement function is realized by the OCT, etc. Further, the axial length measurement function may be used to measure the axial length of the subject's eye by projecting light onto the subject's eye and detecting the returning light from the fundus while adjusting the position of the optical system in the Z direction (front-back direction) relative to the subject's eye. The tonometry measurement function is realized by the tonometer, etc. The OCT function is realized by the OCT apparatus, etc. The ultrasonic inspection function is realized by the ultrasonic diagnosis apparatus, etc. Further, the present invention can also be applied to an apparatus (multifunctional apparatus) having two or more of such functions.

In some embodiments, a program for causing a computer to execute the method of controlling the ophthalmic apparatus is provided. Such a program can be stored in any non-transitory computer-readable recording medium. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

The configurations described in the first to the fifth embodiments can be combined as desired.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic apparatus, comprising:
an objective lens;
an illumination optical system configured to generate illumination light using light from a light source, and to illuminate a subject's eye with the illumination light through the objective lens;
a mounting unit configured to allow an external device including a sensor to be mounted so that the sensor is arranged on an imaging optical path;
an imaging optical system configured to guide returning light of the illumination light from the subject's eye to the imaging optical path;
a communication unit including a transmitter and having a communication function with the external device; and
a controller including processing circuitry configured to control the illumination optical system and to control the sensor through the communication unit to synchronize with control for the illumination optical system,
wherein the illumination optical system includes
a slit in that a slit-shaped aperture is formed, the slit-shaped aperture being capable of being arranged at a position substantially conjugate optically to an imaging site of the subject's eye,
an iris aperture arranged between the light source and the slit, and configured to be capable of being arranged at a position substantially conjugate optically to an iris of the subject's eye, and
an optical scanner deflecting the illumination light that has passed through the aperture, the optical scanner being capable of being arranged at a position substantially conjugate optically to the iris of the subject's eye,
the controller is further configured to control the optical scanner in synchronization with control for the sensor,
the ophthalmic apparatus further comprises an optical element arranged between the light source and the iris aperture, and configured to deflect the illumination light so that the light amount distribution in a direction connecting the aperture formed in the iris aperture and the aperture formed in the slit is maximized, and
the controller is further configured to move the slit in an optical axis direction of the illumination optical system and to change at least one of a position and an orientation of the optical element relative to the aperture formed in the iris aperture.

2. An ophthalmic apparatus, comprising:
an objective lens;
an illumination optical system configured to generate illumination light using light from a light source, and to illuminate a subject's eye with the illumination light through the objective lens;
a mounting unit configured to allow an external device including a sensor to be mounted so that the sensor is arranged on an imaging optical path;
an imaging optical system configured to guide returning light of the illumination light from the subject's eye to the imaging optical path;
a communication unit including a transmitter and having a communication function with the external device; and
a controller including processing circuitry configured to control at least the illumination optical system, under control of the external device through the communication unit,
wherein the illumination optical system includes
a slit in that a slit-shaped aperture is formed, the slit-shaped aperture being capable of being arranged at a position substantially conjugate optically to an imaging site of the subject's eye,
an iris aperture arranged between the light source and the slit, and configured to be capable of being arranged at a position substantially conjugate optically to an iris of the subject's eye, and
an optical scanner deflecting the illumination light that has passed through the aperture, the optical scanner being capable of being arranged at a position substantially conjugate optically to the iris of the subject's eye, the controller is configured to control the optical scanner in synchronization with control for the sensor, the ophthalmic apparatus further comprises an optical element arranged between the light source and the iris aperture, and configured to deflect the illumination light so that the light amount distribution in a direction connecting the aperture formed in the iris aperture and the aperture formed in the slit is maximized, and the controller is further configured to move the slit in an optical axis direction of the illumination optical system and to change at least one of a position and an orientation of the optical element relative to the aperture formed in the iris aperture.

3. The ophthalmic apparatus of claim 1, wherein
the illumination optical system includes an optical modulator configured to be capable of being arranged at a position substantially conjugate optically to an imaging site of the subject's eye, and to generate the illumination light by modulating the light from the light source, and the controller is configured to control the optical modulator in synchronization with control for the sensor.

4. The ophthalmic apparatus of claim 2, wherein
the illumination optical system includes an optical modulator configured to be capable of being arranged at a position substantially conjugate optically to an imaging site of the subject's eye, and to generate the illumination light by modulating the light from the light source, and the controller is configured to control the optical modulator in synchronization with control for the sensor.

5. The ophthalmic apparatus of claim 1, wherein
the illumination optical system includes a first relay lens system arranged between the optical scanner and the slit, and a back focal position of the first relay lens system is a position substantially conjugate optically to the iris.

6. The ophthalmic apparatus of claim 5, wherein
the optical scanner is arranged at the back focal position or the vicinity of the back focal position.

7. The ophthalmic apparatus of claim 5, wherein
the illumination optical system includes a second relay lens system arranged between the slit and the iris aperture, and the iris aperture is arranged at a front focal position of the second relay lens system or the vicinity of the front focal position of the second relay lens system.

8. The ophthalmic apparatus of claim 1, wherein
one or more apertures that the illumination light passes through are formed in the iris aperture so that luminous flux cross section of the illumination light and luminous flux cross section of returning light from the subject's eye are separated on a cornea of the subject's eye, an anterior surface of lens of the subject's eye, and a posterior surface of lens of the subject's eye.

9. The ophthalmic apparatus of claim 8, wherein
two or more apertures are formed in the iris aperture, and
the two or more apertures are formed in linear symmetry to a straight line, the straight line passing through an optical axis of the illumination optical system and extending in a direction corresponding to a longitudinal direction of the aperture formed in the slit.

10. The ophthalmic apparatus of claim 8, wherein
the aperture has a circular segment shape, and
a direction of a chord of the circular segment shape is approximately parallel to a direction corresponding to the longitudinal direction of the aperture formed in the slit.

11. The ophthalmic apparatus of claim 1, further comprising the light source.

12. The ophthalmic apparatus of claim 2, further comprising the light source.

13. The ophthalmic apparatus of claim 1, wherein
the external device includes a light source, and
the mounting unit is configured to allow the external device to be mounted so that the light source is arranged on an optical path of the illumination optical system.

14. The ophthalmic apparatus of claim 1, further comprising
a wavelength selective filter configured to be capable of inserting into or removing from an optical path of the illumination optical system.

15. The ophthalmic apparatus of claim 1, wherein
the external device is a mobile phone or a portable information terminal.

16. The ophthalmic apparatus of claim 2, wherein
the external device is a mobile phone or a portable information terminal.

17. An ophthalmic system, comprising:
an external device including a sensor; and
an ophthalmic apparatus including
an objective lens,
an illumination optical system configured to generate illumination light using light from a light source, and to illuminate a subject's eye with the illumination light through the objective lens,
a mounting unit configured to allow the external device to be mounted so that the sensor is arranged on an imaging optical path,
an imaging optical system configured to guide returning light of the illumination light from the subject's eye to the imaging optical path,
a communication unit including a transmitter and having a communication function with the external device, and
a controller including processing circuitry configured to control the illumination optical system and to control the sensor through the communication unit to synchronize with control for the illumination optical system,
wherein the illumination optical system includes
a slit in that a slit-shaped aperture is formed, the slit-shaped aperture being capable of being arranged at a position substantially conjugate optically to an imaging site of the subject's eye,
an iris aperture arranged between the light source and the slit, and configured to be capable of being arranged at a position substantially conjugate optically to an iris of the subject's eye, and
an optical scanner deflecting the illumination light that has passed through the aperture, the optical scanner being capable of being arranged at a position substantially conjugate optically to the iris of the subject's eye,
the controller is further configured to control the optical scanner in synchronization with control for the sensor,
the ophthalmic apparatus further comprises an optical element arranged between the light source and the iris aperture, and configured to deflect the illumination light so that the light amount distribution in a direction connecting the aperture formed in the iris aperture and the aperture formed in the slit is maximized, and the controller is further configured to move the slit in an optical axis direction of the illumination optical system and to change at least one of a position and an orientation of the optical element relative to the aperture formed in the iris aperture.

18. An ophthalmic system, comprising:

an external device including a sensor; and an ophthalmic apparatus including an objective lens;

an illumination optical system configured to generate illumination light using light from a light source, and to illuminate a subject's eye with the illumination light through the objective lens;

a mounting unit configured to allow the external device to be mounted so that the sensor is arranged on an imaging optical path;

an imaging optical system configured to guide returning light of the illumination light from the subject's eye to the imaging optical path;

a communication unit including a transmitter and having a communication function with the external device; and a controller including processing circuitry configured to control at least the illumination optical system, under control of the external device through the communication unit, wherein the illumination optical system includes a slit in that a slit-shaped aperture is formed, the slit-shaped aperture being capable of being arranged at a position substantially conjugate optically to an imaging site of the subject's eye, an iris aperture arranged between the light source and the slit, and configured to be capable of being arranged at a position substantially conjugate optically to an iris of the subject's eye, and an optical scanner deflecting the illumination light that has passed through the aperture, the optical scanner being capable of being arranged at a position substantially conjugate optically to the iris of the subject's eye, the controller is configured to control the optical scanner in synchronization with control for the sensor, the ophthalmic apparatus further comprises an optical element arranged between the light source and the iris aperture, and configured to deflect the illumination light so that the light amount distribution in a direction connecting the aperture formed in the iris aperture and the aperture formed in the slit is maximized, and the controller is further configured to move the slit in an optical axis direction of the illumination optical system and to change at least one of a position and an orientation of the optical element relative to the aperture formed in the iris aperture.

* * * * *